(12) United States Patent
Muthukumar

(10) Patent No.: US 9,296,263 B2
(45) Date of Patent: Mar. 29, 2016

(54) SMART ACTIVE TYRE PRESSURE OPTIMISING SYSTEM

(71) Applicant: Prasad Muthukumar, Salem (IN)

(72) Inventor: Prasad Muthukumar, Salem (IN)

(73) Assignee: Prasad Muthukumar, Dharmanagar, Suramangalam, Salem, Tamil Nadu (IN)

( * ) Notice: Subject to any disclaimer, the term of this patent is extended or adjusted under 35 U.S.C. 154(b) by 0 days.

(21) Appl. No.: 14/368,192

(22) PCT Filed: Dec. 18, 2012

(86) PCT No.: PCT/IN2012/000826
§ 371 (c)(1),
(2) Date: Jun. 23, 2014

(87) PCT Pub. No.: WO2013/114388
PCT Pub. Date: Aug. 8, 2013

(65) Prior Publication Data
US 2015/0005982 A1 Jan. 1, 2015

(30) Foreign Application Priority Data

Dec. 23, 2011 (IN) .......................... 4539/CHE/2011

(51) Int. Cl.
*B60C 23/00* (2006.01)
*G01N 19/10* (2006.01)
(Continued)

(52) U.S. Cl.
CPC ........... *B60C 23/002* (2013.01); *B60C 23/0408* (2013.01); *B60T 1/10* (2013.01); *B60T 1/16* (2013.01); *B60T 7/22* (2013.01); *B60T 8/1725* (2013.01); *G01B 21/16* (2013.01); *G01L 5/282* (2013.01); *G01L 17/00* (2013.01); *G01M 17/02* (2013.01); *G01N 19/10* (2013.01); *G01P 15/00* (2013.01); *B60T 2201/022* (2013.01); *B60T 2201/03* (2013.01); *B60T 2210/13* (2013.01); *B60T 2230/03* (2013.01)

(58) Field of Classification Search
CPC ......... B60T 2230/03; B60T 7/22; B60T 1/16; B60T 8/1725; B60T 2201/03; B60T 2201/022; B60T 2210/13; B60T 1/10; G01M 17/02; G01P 15/00; G01B 21/16; G01N 19/10; B60C 23/002; B60C 23/0408; G01L 17/00; G01L 5/282
See application file for complete search history.

(56) References Cited

U.S. PATENT DOCUMENTS 5,524,481 A * 6/1996 Claussen et al. ............. 73/146.3
2002/0095253 A1* 7/2002 Losey et al. ..................... 701/71
(Continued)

*Primary Examiner* — Rodney Bulter

(57) ABSTRACT

Smart Active Tire Pressure Optimizing System is a highly time sensitive design and technique that acts instantaneously to sense and control the tire pressure particularly during imminent/inevitable critical driving situations to reduce emergency and high speed breaking distance, mitigates loss of traction, hydroplaning, roll over, loss of stability, over and under steering, brake-failure, loss of control due to puncture through real-time sensing, perform context aware computing and directing Tire Pressure Control Units to actively control the tire pressure in right time with right pressure on right tires thereby instantly controlling footprint and sidewall deformation rate to enhance, traction and stability simultaneously sustaining drivability/steer-ability and restore/optimize to pre-set tire pressure value immediately after overcoming critical situation for further safe and comfortable driving. Other aspects are controlling tire temperature according to environmental temperature, moisture and humidity to enhance traction and vary tire pressure according to driving modes like comfort, standard, sports etcetera.

24 Claims, 6 Drawing Sheets

(51) Int. Cl.
*G01P 15/00* (2006.01)
*G01B 21/16* (2006.01)
*G01L 17/00* (2006.01)
*G01M 17/02* (2006.01)
*G01L 5/28* (2006.01)
*B60C 23/04* (2006.01)
*B60T 1/10* (2006.01)
*B60T 1/16* (2006.01)
*B60T 7/22* (2006.01)
*B60T 8/172* (2006.01)

(56) References Cited

U.S. PATENT DOCUMENTS

| | | | |
|---|---|---|---|
| 2002/0157461 A1* | 10/2002 | Schmidt et al. | 73/146 |
| 2003/0230443 A1* | 12/2003 | Cramer et al. | 180/65.5 |
| 2004/0107042 A1* | 6/2004 | Seick | 701/117 |
| 2004/0212486 A1* | 10/2004 | Dinello et al. | 340/445 |
| 2006/0145828 A1* | 7/2006 | Muller et al. | 340/442 |
| 2006/0180256 A1* | 8/2006 | Mittal | 152/416 |

* cited by examiner

FIG – 3
HIGH PRESSURE RESERVOIR CONFIGURATIONS
FIG – 3A
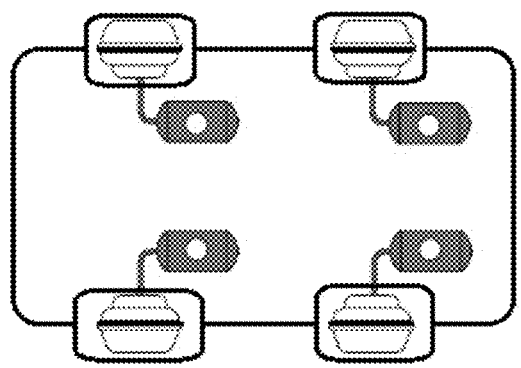
FIG – 3B
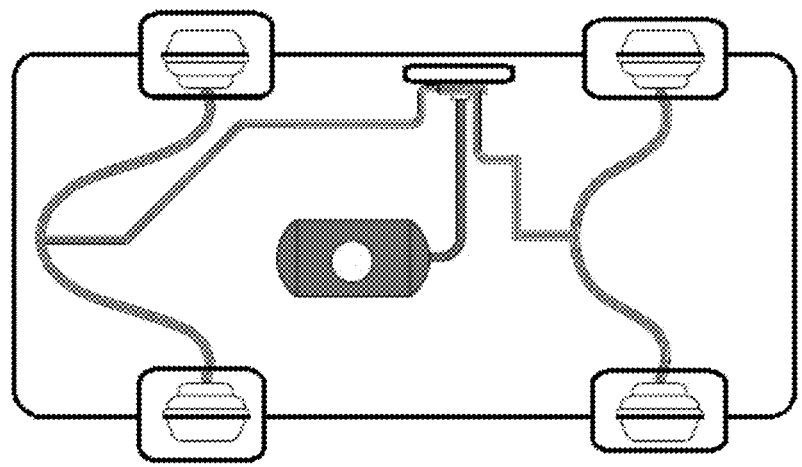

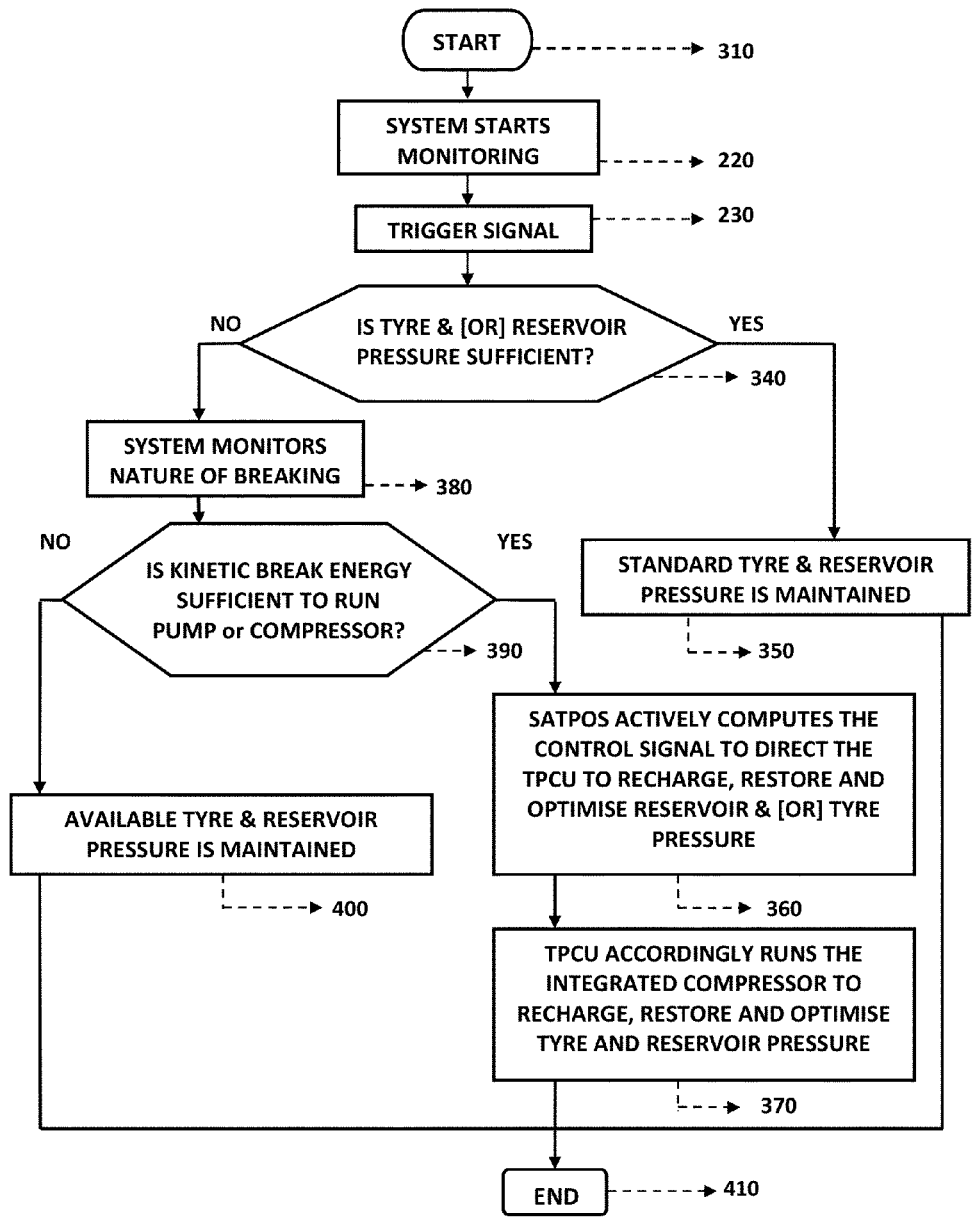

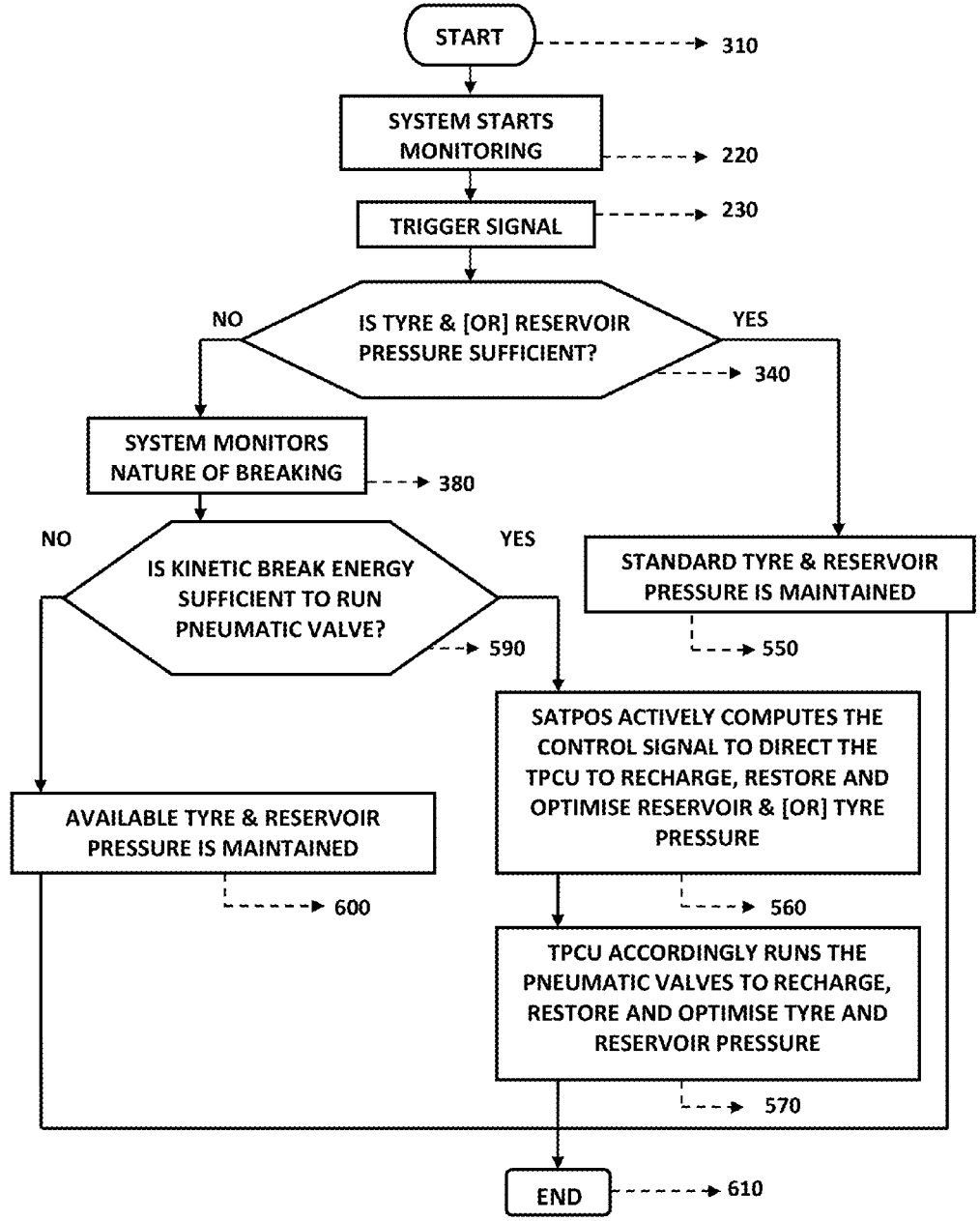

FIG – 6
FIG – 6A
SATPOS UTILISING KINETIC BREAK ENERGY TO RUN THE PUMP OR COMPRESSOR
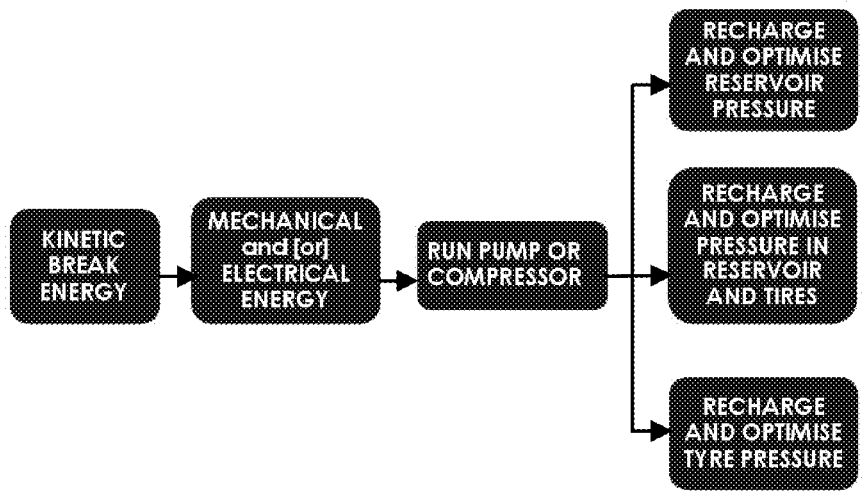
FIG – 6B
SATPOS UTILISING KINETIC BREAK ENERGY TO RUN THE PNEUMATIC VALVES FOR FLUID TRANSFER
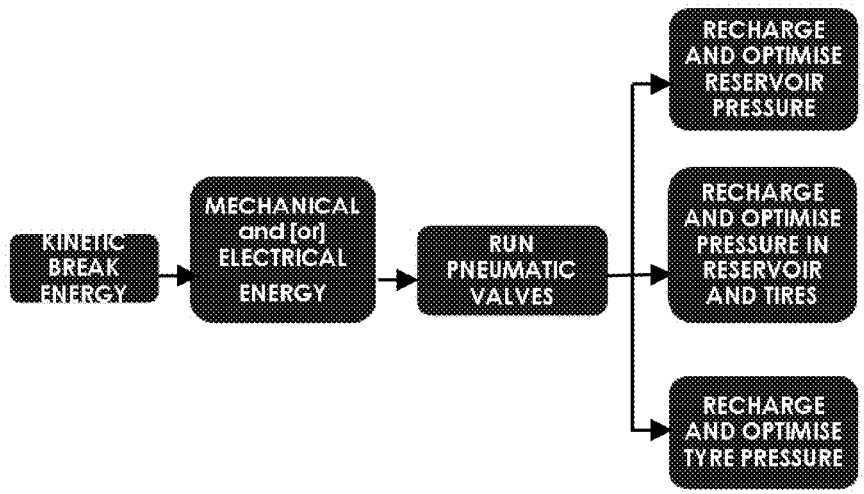

SMART ACTIVE TYRE PRESSURE OPTIMISING SYSTEM

FIELD OF INVENTION

Smart Active Tyre Pressure Optimizing System (SATPOS) is related to automobile or transportation domain and more particularly into vehicles utilising pneumatic tires.

BACKGROUND OF INVENTION

Tyre pressure plays an important role in vehicle traction and stability.

REFERENCES CITED AND PRIOR ART

1. US 2007/0044881 A1 (STEYR-DAIMLER-PUCH SPEZIALFAHRZEUG GMBH) 1 Mar. 2007 description, paragraphs [0001], [0012], [0020]-[0030] and FIG. 1.
2. US 2003/0230342 A1 (STEYR-DAIMLER-PUCH SPEZIALFAHRZEUG AG & CO. KG) 18 Dec. 2003 the whole document.
3. US 2011/0203710 A1 (MESA DIGITAL, LLC) 25 Aug. 2011 the whole document.
4. WO 2011/004229 A1 (NISSAN MOTORS CO., LTD) 13 Jan. 2011 the whole document.
5. CN 101927667 A (CHERY AUTOMOBIILE CO., LTD) 29 Dec. 2010 the whole document.
6. CN 202080074 U (SHANDONG UNIVERSITY OF TECHNOLOGY) 21 Dec. 2011 the whole document.

Generally the vehicles tyre pressure are manually set to an optimum value or Tyre Pressure Control System (TPCS) works to maintain set pressure value to enhance driving on various terrains, better mileage, enhance driving comfort, reduced—tyre noise, friction, wear and tear etcetera. But maintaining these optimum or set pressure (fixed value) values constantly irrespective of the critical situations (which won't vary tyre pressure instantaneously according to critical situations) in turn doesn't helps in enhancing the vehicles available traction and stability in critical situation. For example, in critical situations these constantly maintained optimum or set tyre pressure values only sustains the available traction & stability of corresponding pressure value which won't help in improving traction and stability (rolling resistance, friction etcetera) thereby to reducing emergency braking distance, won't help in mitigating hydroplaning (by increasing tyre thread depth to deflect more water outward thereby helping in clearing water), won't aid to mitigate roll over or loss of vehicle stability by controlling tyre pressure (for vehicle moving in highly uneven, slope surfaces, vehicles experience extreme cornering force etcetera where the vehicle tends to move beyond available stability systems limits that can leads to loss of stability), doesn't mitigate over and under steering (by controlling tyres cornering stiffness, controlling tyre deformation rate, contact patch or foot print to increase traction, mitigate positive and negative gradient to sustain a neutral gradient) etcetera. Maintaining constant tyre pressure in particularly during critical situations only sustains available traction and won't help in enhancing high speed and emergency braking efficiency by improving traction (rolling resistance, friction etcetera) thereby to reducing emergency braking distance. The ABS and TCS can prevent loss of traction from happening by limiting power to the wheels. During critical situations ABS (Antilock Braking System U.S. patent Ser. No. 07/216,918 and Ser. No. 10/213,565) and TCS (Traction Control System U.S. patent Ser. No. 12/359, 942) only prevents wheel lock and loss of traction from happening by limiting power to the wheels. So the ABS and TCS doesn't increase the much needed actual vehicle traction in critical situations, but are only the techniques to utilise the available traction efficiently. The ESC detects loss of steering control and automatically applies the brakes (selective wheel braking, which in turn depends on road contact) to help in steering the vehicle where the driver intends to go. Braking is automatically applied to wheels individually, such as the outer front wheel to counter over steer or the inner rear wheel to counter under steer. Some of the ESC systems also reduce engine power until control is regained. But in critical situations, these ESC systems cannot increase the limits of much needed available tyre traction and is used only to decrease the effect of driver error or compensate for a driver's inability to react quickly enough to wheel slip. The ESC works with the available traction (between the tyres and road) and is not so effective in severe hydroplaning scenario (as the wheels that ESC would use to correct a skid may not even initially be in contact with the road, reducing its effectiveness). So the ESC can help to regain the control but cannot mitigate aquaplaning. Maintaining constant tyre pressure won't help in mitigating hydroplaning (by increasing tyre thread depth to deflect more water outward thereby helping in clearing water). Aquaplane or hydroplaning occurs when the tyres (grooves) cannot remove water quickly enough which in turn leads to loss of contact with the road surface and skims across the top of the standing water. Hydroplaning happens more easily with lack of tyre tread depth, under inflation which causes a tyre to deflect water inward thereby raising the tyre centre and preventing the treads from clearing water. Maintaining constant tyre pressure won't aid to mitigate roll over or loss of vehicle stability by controlling tyre pressure (for vehicle moving in highly uneven, slope surfaces, vehicles experience extreme cornering force etcetera where the vehicle tends to move beyond available stability systems limits which can leads to loss of stability).

There are some tyre pressure control systems that only works to maintain optimum or set tyre pressure value throughout the period of time (that won't change according to critical situations) which only helps to enhance driving on various terrains and won't sense critical situations or instantly vary or control the maintained tyre pressure thereby to aid the vehicle to overcome the critical situations like—emergency braking, hydroplaning, loss of traction, loss of stability or roll over mitigation, over and under steering mitigation etcetera. There are scenarios where the fixed optimum and pre-set terrain based tyre pressure control system (used enhancing driving in various terrains which maintain constant pressure irrespective of critical situation like hydroplaning) that won't help in mitigating hydroplaning. During emergency braking the tyre traction can also vary based on contamination between tyres and road surfaces (contact area) like layer of water, sand etcetera which can causes significant loss of traction and the tyre pressure control system won't works in sensing and mitigating these scenarios. More particularly the slow processing and functioning speed of the other Tyre Pressure Control Systems (TPCS) won't work or help in critical situations as these scenarios are highly time sensitive that requires instant processing and functioning. Also other systems that utilise vehicles with integrated or inbuilt compressor and similar systems have lot of complications as it consumes the valuable space and power also adding extra weight to the vehicle which makes the SATPOS more expensive, complex to—operate, integrate, maintain and service that prevents it from large-scale implementation.

OBJECTIVE OF INVENTION

Objective of the invention is to enhance vehicle traction and stability in critical driving situations like emergency braking distance, avoid or mitigate—loss of traction, hydroplaning, roll over or loss of stability, inevitable collision, over and under steering through instantaneously controlling tyre pressure ultimately to protect the vehicle, occupants, pedestrians and other things around or on the way by preventing or reducing the impact of collision.

SUMMARY

To address the issues with optimally maintaining tyre pressure constantly all over the time and other non-time sensitive tyre pressure control systems, the SATPOS provides a smart active tyre pressure optimizing system that instantaneously works in critical situations by sensing, computing and controlling the tyre pressure on right tyres with right pressure in right time according to critical situations thereby to enhance the available traction and stability. The SATPOS aids in enhancing and effectively optimizing vehicles overall performance in safety, stability, control, speed, mileage, reducing tyre wear & tear and impact on environment. The critical situations won't occur always but can occur at any time as a surprise and the SATPOS constantly monitors and equipped to face the challenges placed ahead thereby helps in overcoming or mitigating the critical driving situation ultimately protecting the passengers, pedestrians, vehicles and other objects in and around the way. Even an inch to a meter distance is crucial in extreme situations to avoid, mitigate and reduce the impact of collision that in turn helps in saving valuable lives and property. The SATPOS 102 performs active sensing, pre-computing & set ready to control the tyre pressure prior to critical situation, current-computing for controlling the tyre pressure during critical situation, post-computing to optimize tyre pressure after overcoming the critical situation ultimately to overcome and mitigate the critical situations. The SATPOS mainly controls the tyre pressure between upper and lower cut-off tyre pressure values with corresponding change in vehicles load and centre of gravity thereby mitigating critical situations simultaneously preventing over and under inflation ultimately to sustain stability. SATPOS utilise smart and adaptive closed loop processing algorithm with predetermined and tested lookup table to instantaneously check and compare the effects between predetermined and tested real world scenarios to the actual real world scenarios for actively sensing, computing and controlling the tyre pressure in right time on right tyres with right pressure thereby to mitigate the critical situations. Besides alerting the driver regarding the controlling of tyre pressure the SATPOS also optimizes the tyre pressure once the vehicle overcomes the critical situation to continue with optimal driving. Since various parameters and multiple critical situations are simultaneously taken into account by SATPOS for computation, the SATPOS's algorithm smartly sense, prioritise & balance between to achieve an optimized solution. The SATPOS works in standalone mode based on sensor system parameters or in addition interoperate with vehicles safety and stability systems to further enhance the efficiency of ABS, EBD, ESC, TCS, BA, suspension system, roll over mitigation system, automotive aerodynamics & airbrakes etcetera thereby enhancing the overall performance in sustaining traction and stability. As most of the parameters utilised by SATPOS are already available with vehicles; which in turn aids in easy implementation of SATPOS. SATPOS in addition to instantaneously varying and controlling the tyre pressure in critical situations also immediately optimizes or restores the tyre pressure if difference or variation in tyres pressure is detected from the optimum or pre-set pressure value once the vehicle overcomes the critical situations to continue with safe & comfortable driving with enhanced stability, mileage and to reduce tyre noise. According to design, configuration and scenarios the SATPOS either controls the pressure by releasing the fillers to atmosphere while maintaining the tyres lower cut off threshold pressure value to sustain stability and instantaneously optimize the pressure on all tyres for further safe driving (till next gas station or filling) until restoration or else restores the pressure to optimum pre-set value utilising in inbuilt reservoir or other external restoration systems immediately after the vehicle overcomes critical situation to continue with comfortable driving. The SATPOS works in standalone mode or interoperate with vehicles safety and stability systems or its combinations according to design, configurations and scenarios. Either dedicated hard or soft or its combinations SATPOS switches are utilised for manually activate SATPOS. The following aspects are flexible as either basic to higher end, one or multiple or combination of following aspects are utilised according to design, configurations, requirements and scenarios.

According to one aspect, the SATPOS instantaneously works in critical situation to reduce high speed and emergency braking distance by actively sensing, computing and controlling the tyre pressure to some extent from optimum or existing value to right pressure on right tyres in right time ultimately to increase the rolling resistance and friction thereby instantaneously improving traction while sustaining stability. The SATPOS maintains the tyres upper & lower cut-off threshold pressure values to prevent over inflation and under inflation or tyre deformation.

According to another aspect, the SATPOS instantaneously mitigates the extreme loss of traction, skid and wheels spin on either one or multiple wheel tyres by actively sensing, computing and controlling the tyre pressure between or corresponding tyres in right time with right pressure thereby to restore and mitigate loss of traction.

According to another aspect, the SATPOS instantaneously mitigates hydroplaning or aquaplaning by actively sensing, computing and controlling (increasing) the tyre pressure on right tyres with right pressure on right time while maintaining the tyres upper cut-off threshold value to reduce the surface area of tyre to avoid water deflected inwards, increasing the tyres grooves & thread depth to deflect more water outward thereby helping in clearing water which in turn prevents the rising of tyres thereby to restoring traction and mitigating aquaplaning.

According to another aspect, the SATPOS instantaneously works to mitigate over and under steering by actively sensing, computing and controlling the tyre pressure in right time with right pressure on right tyres thereby controlling thread depth, enhancing traction, controlling contact patch or foot print, controlling tyres cornering stiffness and controlling tyre deformation thereby mitigating positive and negative gradient to sustain zero or neutral gradient.

According to another aspect, the SATPOS instantaneously mitigate roll over and loss of stability by actively sensing the vehicle (moving with hard cornering and in surface like highly uneven, inclined, slope etcetera) that tend to move beyond available stability systems limits thereby computing and controlling the tyre pressure in right time with right pressure on right tyres thereby to sustain stability.

According to another aspect, the SATPOS mitigates the loss of control & stability in puncture scenario (besides alerting the driver regarding rapid loss of pressure in puncture scenarios) by actively sensing and instantaneously supplying the fillers [air or nitrogen] from the reservoir to the punctured tyres thereby to sustain the pressure preventing the rapid loss of tyre pressure ultimately improving the time of drivability and stability of the vehicle.

According to another aspect, the SATPOS instantaneously works to enhance extreme and high speed-cornering (hard cornering) performance, torque vectoring and handling characteristic by instantaneously sensing, computing and controlling the tyre pressure in right time with right pressure on right tyres thereby assist in sharp cornering, preventing tyres sidewall deformation simultaneously optimizing traction and stability.

According to another aspect, the SATPOS vary, control and optimize the tyre pressure according to driving modes like comfort, comfort+, standard, economic, sport, sport+ modes etcetera to enhance the comfort level, performance, improving fuel efficiency thereby reducing effect on environment, controlling tyre noise according to modes and also works irrespective of modes in instantaneously controlling the tyre pressure according to critical situations. According to design, configuration and scenarios the SATPOS either controls the tyre pressure by releasing the fillers to atmosphere or utilise inbuilt reservoir or other external restoration systems or its combinations.

According to another aspect, the SATPOS works to control and optimize the tyre pressure according to change in centre of gravity and load on each wheel tyres by sensing, computing and controlling or optimizing the tyres accordingly to enhance the vehicle stability and handling characteristic.

According to another aspect, the SATPOS particularly utilises one or more high pressure reservoirs or tanks for storing the fillers like air and nitrogen that are optimally located (mounted) or integrated on wheel's rim, spoke's, hub, axle etcetera with pneumatic valve and control system for controlling the tyre pressure in critical situations and optimizing or restoring the tyre pressure during and after overcoming the critical situations according to the control signal from the SATPOS. These reservoir systems operates without any compressor or similar sources as the pressure maintained in the reservoir is higher (multiple times) than the optimum tyre pressure for the fluids or fillers to flow from reservoir to tyre thereby controlling the tyre pressure accordingly and the fillers are restored through external sources.

According to another aspect of SATPOS, the TPCU comprises of integrated compressor or pump powered by kinetic brake energy in combination with high pressure fluid reservoir to recharge reservoir fluid and in turn the reservoir restores the tyre pressure or without high pressure reservoir system for directly recharging tyre pressure or its combinations based on design, configuration and scenarios thereby to restore and optimize the tyre pressure ultimately to provide maintenance free operation of tires. The users don't need to maintain or restore the tyre pressure as the SATPOS itself will autonomously work to recharge and maintain the optimum tyre pressure.

According to another aspect of SATPOS, the TPCU utilise kinetic brake energy to run the pneumatic valves thereby to control or transfer the fluid such as air, nitrogen etcetera flow from & to or between atmosphere, pump, compressor, reservoirs and tyres or its combinations according design, configuration, requirement and scenarios ultimately to restore and optimize the tyre and reservoir pressure.

According to another aspect of the SATPOS, in an extreme worst case scenario that comprising of malfunction, partial or complete failure of vehicle safety and stability system (Example—failure of brakes, TCS, rollover mitigation system etcetera) occurs either the on-board system automatically sense the failure to trigger SATPOS or the SATPOS is manually triggered to instantaneously control the tyre pressure for increasing the friction, traction and rolling resistance ultimately to reduce the stopping distance while simultaneously maintaining the vehicle stability, drivability and steer-ability thereby mitigating critical situations.

According to another aspect of SATPOS, the TPCU 104 integrated with Active Tyre Temperature Optimizer System (ATTOS) that works to control and maintain the tyre temperature and pressure according to change in temperature of weather or environment and critical situations thereby controlling the tyres property, softening, hardening or solidification and sidewall deformation rate ultimately to enhance tyre traction, reduce braking distance (emergency or normal according to scenario), enhance cornering & handling characteristics, mitigate hydroplaning, mitigate over and under steering etcetera. The ATTOS controls the tyre temperature instantaneously in critical situation or continuously according to design, configuration and scenarios.

According to another aspect, the SATPOS utilise inbuilt sensor system to actively scan, sense, compute and alerts the driver irrespective of vehicles in motion or stationary regarding wheels or rims structural damage comprising of bends & cracks and potentially hazardous foreign objects (Example—stones) stuck in tyres based on its nature, dimension & depth of penetration, tyres wear & tear, tyre cuts, bulges, sidewall damages, slow puncture with corresponding tyres location & position.

BRIEF DESCRIPTION OF THE DIAGRAM

To get a comprehensive understanding of the SATPOS, diagrams are described by examples.

FIG. 3 illustrates the SATPOS with various reservoir configurations. One 3A with centralised reservoir system and another 3B with dedicated reservoir system.

FIG. 4 illustrates the flowchart and describes the method of operation of the SATPOS utilising Kinetic Brake Energy to run pump and compressor.

FIG. 5 illustrates the flowchart and describes the method of operation of the SATPOS utilising Kinetic Brake Energy to run Pneumatic valves.

Figure 1:
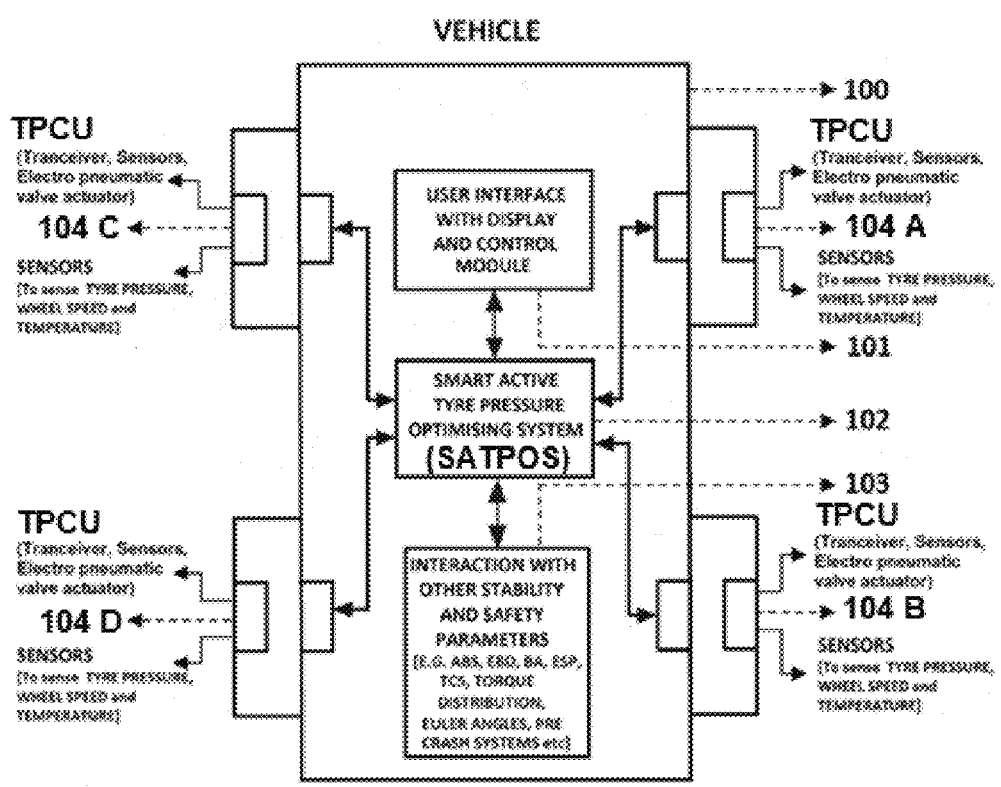
FIG. 1 illustrates the block diagram of SATPOS comprising of components according to Smart Active Tyre Pressure Optimizing System (SATPOS), Tyre pressure Control Unit (TPCU), User Interface, Interaction with other sensor systems, ECU, safety and stability systems

FIG. 6 [A&B] illustrates the block diagram of SATPOS that describes the method of operation of the SATPOS utilising Kinetic Brake Energy to run pneumatic valves, pump and compressor.

DETAIL DESCRIPTION

The SATPOS works by actively sensing critical situations and computing the tyre pressure in real time based on parameters comprising of sensor system, vehicle stability & safety systems, nature of braking & brake force, tyres lower & upper cut-off threshold pressure values, sensing reservoirs and tyres internal & external or environmental—pressure, temperature, moisture, humidity, vehicles speed, wheel speed, acceleration & deceleration, orientations & axial rotation (yaw, pitch and roll), load distribution (load on each wheel tire), torque distribution, vehicles suspension & vertical dynamics, transverse motion & lateral acceleration, tyre traction, Coefficient of Friction (COF), slip and slide angle, steering wheel position, cornering effects, change in centre of gravity, over & under steering, aqua or hydroplaning, radars detecting objects with pre-computing & current-computing of tyre pressure to assist in emergency braking & stability based on range, direction and dimension of objects in and around the vehicle, rim or wheel specifications, tyre specifications & parameters comprising of—size, type, load index, speed symbol or rating, thread wear & tear, traction & temperature rating, tyres dimension, direction, compound & material used, maximum load rating, maximum permissible inflation pressure, patterns of treads, lugs, voids, sipes & groves, wheel alignment & balancing, camber angle, Tyres position or angle of attack, sensing nature of tyres present & impending contact area (road sensing), GPS information to predict the turns, curves and bends on roads ahead and inter operating with vehicles existing stability & safety systems comprising of Anti-lock Braking System (ABS), Electronic Brake-force Distribution (EBD), Electronic Stability Control (ESC), Traction Control System (TCS), Roll over mitigation systems, Engine Control Unit (ECU), Brake Assist (BA), Pre-crash systems, suspension system, vertical dynamics & damping force, Sway or anti-roll or stabilizer bar, radar assisted auto braking with partially & complete brake to stop, automotive aerodynamics & airbrakes, sensing Drivers reaction with evasion (evasive manoeuvre) of objects, Cruise or Adaptive Cruise Control with partial & full auto braking; thereby instantaneous direct the TPCU to control the tyre pressure on corresponding tyres in right time thereby to overcome or mitigate the critical situations. As various parameters and multiple critical situations are simultaneously taken into account by SATPOS for computation, the SATPOS algorithm smartly sense, prioritise and balance between one or more parameters and scenarios to achieve an optimized solution. The design actively monitors the status of the SATPOS and their component thereby updates the driver in real time. Also mainly alerts the driver in case of the SATPOS is active and functioning through user interface regarding SATPOS's operations in critical situations comprising of controlling the tyre pressure, TPCU's lower power reserve; availability & lack of fillers in reservoir, component failure, temperature controlling status, potentially hazardous object stuck in tyres etcetera according to design, configuration and scenarios. The SATPOS performs self-diagnostic or test to verify and conform regarding working of components and accessibility of corresponding parameters; in case of crucial parameters inaccessible and components failure the SATPOS will operate in fail-proof or fail-safe mode and default mode to ensure safe operation. Based on configurations the testing are performed automatically (like whenever the vehicle is started, in a set or schedules timings etcetera) and manually. The controlling of pressure is either even or uneven & continuous or discontinuous on all tyres according to design, configurations, critical situations and scenarios. The SATPOS utilise either utilise wireless transceiver which is a combination of transmitter and receiver with antenna or wires for communication between SATPOS and TPCU. The TPCU utilise fail-safe and fail-proof pneumatic valves system with actuators for controlling the tyre pressure according to control signal from SATPOS. The TPCU comprise of and utilise wheel tyres integrated with single to multiple internal and external, unidirectional and bidirectional, valves with & without actuators, normally open & normally closed valves, basic & electro pneumatic valves, dedicated & common valves for storing, controlling, optimizing and restoring the tyre pressure according to design, configurations and scenarios. The SATPOS sense the valve connected with external sources for restoring the filers and the valves works with basic valve function in scenarios of absence and low power reserve. The SATPOS also helps in enhancing the tyre performance where the driver is not in a feasible situation to change the tyres to adopt according to environment or scenarios like usage of different environment specific tyres (like dry tires, wet tires, all terrain tires, summer tires, winter tires, snow tyres etcetera), all weather tyres and even enhancing performance of worn tyres that are about to reach tread wear bar or indicator. TPCUs are optimally designed, compact, highly reliable, withstand mechanical stress, pressure and temperature are located on each wheel tires. The TPCU can be integrated or hidden in the spokes of the wheels for protection and to better the appearance. As the SATPOS substantially utilises and interoperate with most of the vehicles already existing sensor systems, safety and stability parameters which helps in easy implementation of the SATPOS.

FIG. 1 is a block diagram describing the working principle and various integral components of the SATPOS on vehicle 100 according to the SATPOS comprising of Tyre pressure Optimizing System 102, Tyre Pressure Control Units 104 ABC&D, user interface with display and control unit 101, Interaction with vehicle's ECU, safety and stability parameters 103 etcetera. The SATPOS 102 is the centralised system that computes and controls all the TPCU's 104. The SATPOS performs active monitoring & sensing, pre-computing & set ready to control the tyre pressure prior to critical situation, current-computing for controlling the tyre pressure during critical situation, post-computing to optimize tyre pressure after overcoming the critical situation ultimately to overcome and mitigate the critical situations. Information and control signals are transmitted and received in a periodic and continuous manner through wired—and wireless communication network between SATPOS 102 and TPCU'S 104 regarding the status of the components and parameters according to design, configuration and scenarios. The processing unit utilise adaptive closed loop processing algorithm with predetermined and tested correlation or lookup table to instantaneously check and compare the effects between predetermined and tested real world scenarios to the actual real world scenarios for smart & actively sensing, computing and controlling the tyre pressure in right time on right tyres with right pressure thereby to mitigate the critical situations. The TPCU's 104 control the tyre pressure and temperature according to the control signal from SATPOS. The processing unit SATPOS 102 computes the control signal based on the real time parameters form sensor systems, TPCU, ECU, vehicle Safety & stability systems, predetermined & tested parameters also accounting user interface 101 with corresponding configurations. According to control signal from SATPOS 102 the TPCU'S 104 instantaneously controls the tyre pressure on right tyres with right pressure in right time and varies tyre temperature thereby to enhance traction and stability. The TPCU comprise of sensors, pneumatic valves and electro pneumatic valve actuators (Solenoid actuated value, pneumatic, piezo electric etcetera), sensor system, control circuitry, transceiver, antennas, Active Tyre Temperature Optimizing System (ATTOS), heating elements, power source, reservoir, moisture control system, air filter etcetera and actively shares the sensor system parameters and components status with the SATPOS 102. Each TPCU's 104 has an unique identifier (Signal ID) to identify, transmit & receive information with SATPOS 102 and are located (mounted) on all wheel tyres representing corresponding wheel tyres with its position that are utilised by SATPOS for centralised management of all TPCU's 104. The reservoir design utilise moisture control system to remove excess moisture and maintain optimum moisture level of fillers in reservoir thereby to achieve optimum SATPOS operations. The SATPOS 102 learns, detects and saves the ID's of TPCU's 104 on each wheel tyres with the location or position and the learning process for is both automatic and manual configurable according to design and scenarios which also accounts changed or rotated tires. The SATPOS 102 detects and transmits the computed control signal (pressure and temperature values) to corresponding TPCU's 104 based on the unique ID's. Once the learning process is completed and synchronised the SATPOS starts monitoring and controlling the TPCU's 104, which are further wired into control and display units. At any time when the engine is on & running or off, the SATPOS 102 according to design, configurations and scenarios monitor's signals from TPCU's and updates the status for active computing and controlling. The controlling of tyre pressure is preformed either simultaneously on all the tyres or any particular tyres according to scenarios. Both SATPOS 102 and TPCU 104 contain Transceiver which is a combination of transmitter and receiver with antennas for communication. The SATPOS works either in wireless and wired mode according to designed, configuration and requirement. TPCU 104 comprise of provision to enable and disable on spare tyres. The SATPOS also accounts the turbulence created during controlling of tyre pressure and thereby accordingly controls the tyre pressure to compensate the turbulence based on scenarios.

According to one aspect, the SATPOS 102 actively sense high speed & emergency braking situations thereby immediately compute and direct the TPCU 104 to instantaneously control the tyre pressure from optimum or existing value to right pressure on right tyres in right time to enhance traction and rolling resistance thereby reducing braking distance while sustaining stability ultimately to protect the vehicles, occupants, pedestrians and other things around or on the way. In high speed and emergency braking, the braking distance is influenced by the tyre traction which in turn is also mainly influenced by tyre pressure. SATPOS works based on—maintaining the tyres upper and lower cut-off value to avoid tyre deformation and over inflation of tires, sensor system parameters, suspension, vehicle safety and stability parameters ultimately to reduce the braking distance simultaneously sustaining the vehicle stability. Instantaneously reducing the tyre pressure to some extent increases the rolling resistance and friction by controlling the contact patch or foot print which in turn increases the rolling resistance and traction there by reducing the high speed & emergency braking distance. SATPOS restores and optimizes the tyre pressure immediately after the vehicle overcomes the emergency braking situation to continue with safe and comfortable riding.

According to another aspect, the SATPOS 102 actively sensing the loss of traction, skid & wheel spin thereby immediately compute and direct the TPCU 104 to instantaneously controls the tyre pressure on right tyres (between wheels tyres that experiencing loss of traction (wheel spin) and the wheels that have traction) with right pressure to restore traction thereby to mitigate loss of traction and wheel spin. Generally TCS acts as secondary function of ABS and are designed to prevent loss of traction. Traction control system works to prevent loss of traction from happening by limiting power to the wheels through applying brake force at one or more wheels, reducing or suppressing spark sequence to one or more cylinders, reducing fuel supply to one or more cylinders, closing the throttle (if the vehicle is fitted with drive by wire throttle), in turbo-charged vehicles a boost control solenoid are actuated to reduce boost and therefore engine power etcetera. So in critical situations the TCS cannot so increase the limits of friction or grip and works with available wheel tyres traction thereby only used to decrease the effect of driver error or compensate for a driver's inability to react quickly enough to wheel slip. But the SATPOS either works in standalone mode or interoperates with Traction Control System thereby controlling the tyres contact patch or foot print to enhance the available traction in critical situations ultimately further enhancing the efficiency of TCS. SATPOS restores and optimizes the tyre pressure immediately after the vehicle overcomes loss of traction to continue with safe and comfortable riding.

According to another aspect, the SATPOS 102 actively mitigates hydroplaning or aquaplaning by sensing, computing and directing the TPCU 104 to instantaneously control (increasing) the tyre pressure in right tyres with right pressure on right time while maintaining the tyres upper cut-off threshold value thereby enhancing the grooves and threads to disperse more water beneath the tyres to restore traction. The ESC can help to regain the control but cannot mitigate aquaplaning. Although bald tyres give better grip on dry roads than treaded tires, they are unsafe in rain as the efficiency of these tyres in removing water between tyres and contact area is low. Thread depth plays an important role in mitigating hydroplaning and the SATPOS works instantaneously enhancing the thread depth thereby reducing the surface area of tyres to avoid water deflected inwards, increasing the tyres thread depth to deflect water outward ultimately helping in clearing water which in turn prevents the rising of tyres to restoring traction and mitigate aquaplaning. SATPOS even helps in enhancing the wet traction efficiency of worn tyres that are about to reach tread wear bar or indicator. The SATPOS detects hydroplaning by sensing loss of traction (slip), increase in wheel spin, vehicle stability, contact area or road sensing parameters (to sense the property of road wet, dry etcetera), sensing vehicle accelerate at higher rate than the intended speed, vehicles direction, sudden rise in engine RPM due to wheel spin without traction, load on wheel tires, nature of drivers input like acceleration and braking etcetera; thereby computing and directing the TPCU to control the pressure on right wheels with right pressure in right time to mitigate aquaplaning and restore vehicles traction. SATPOS restores and optimizes the tyre pressure once the vehicle overcomes aquaplaning to continue with safe and comfortable riding.

According to another aspect, the SATPOS 102 instantaneously works to mitigate over and under steering. ESC detects loss of steering control and traction thereby automatically apply the brakes on wheels individually (selective wheel braking) such as the outer front wheel to counter over steer or the inner rear wheel to counter under steer ultimately to help "steer" the vehicle where the driver intends to go. Some ESC systems also reduce engine power until control is regained; but these ESC and similar systems works with available traction and cannot enhance the available tyre traction. Generally over and under steering are caused by loss of traction tyres and the SATPOS works by actively sensing, computing and directing the TPCU 104 to instantaneously control the tyre pressure in right time with right pressure on right tyres thereby controlling thread depth, enhancing traction, controlling contact patch or foot print, controlling tyres cornering stiffness and controlling tyre deformation rate thereby mitigating positive and negative gradient to sustain zero or neutral gradient. SATPOS either works in standalone mode or interoperates with vehicles safety and stability systems like ESC, ESP, DSC, TCS, suspension etcetera to enhancing the performance. SATPOS restores and optimizes the tyre pressure immediately after the vehicle overcomes under and over steering to continue with safe and comfortable riding.

According to another aspect, the SATPOS 102 actively sense the roll over & loss of stability thereby immediately computing and directing the TPCU 104 to instantaneously control the tyre pressure in right time on right tyres with right pressure to restore or mitigate roll over and loss of stability ultimately to sustain stability. When the vehicle tends to roll generally the Electronic stability control, roll over mitigation systems, suspension etcetera and other related systems works to certain extent to mitigate roll over. But there are certain scenarios where the vehicles tends to go beyond the extreme roll over limits of these systems like vehicle moving around on highly uneven terrain, leaning, slope surfaces, vehicle experiencing extreme cornering force like entering with high speed in tight corners etcetera that can leads to loss of stability. SATPOS sense the limits beyond which roll over is imminent or inevitable thereby accordingly controls the pressure on right tyres with right pressure on right time thereby to improve stability, centre of gravity and traction. SATPOS won't interrupt the vehicle tyre pressures until the vehicle is about to reach the limit beyond which the vehicle will tend to roll. The SATPOS works in standalone mode or interoperates to enhance the performance of ESC, rollover mitigation systems etcetera. SATPOS restores and optimizes the tyre pressure immediately after the vehicle overcomes the critical situation to continue with safe and comfortable riding.

According to another aspect, the SATPOS 102 works in critical situations to mitigates the loss of control and stability in puncture scenarios (besides alerting the driver regarding rapid loss of pressure in puncture scenarios) by actively sensing and directing the TPCU 104 to instantaneously supply the fillers like air or nitrogen from the reservoir or tank to the punctured tyres thereby to sustain the pressure preventing the rapid loss of tyre pressure ultimately improving the time of drivability and stability of the vehicle. Loss of pressure in punctured tyres leads to high or difference in rolling resistance and traction than other tyres which comparatively comprise of least rolling resistance and traction that in turn leads to loss if vehicle stability and steer ability or drivability. So the SATPOS actively works to control tyre pressure ultimately to control the rolling resistance and traction of the other tyres in accordance with punctured tyres to mitigate difference in rolling resistance and traction levels. Besides controlling the tyre pressure on punctured tyres the SATPOS also controls (reduce) the pressure on other tyres according to scenarios to enhance the vehicles drivability, stability and increasing the rolling resistance thereby reducing the braking distance of vehicles in high speeds. As the loss of pressure in punctured tyres leads to high or difference in rolling resistance and traction than other tyres which comparatively comprise of least rolling resistance and traction that in turn leads to loss if vehicle stability and steer ability or drivability. So the SATPOS actively works to control tyre pressure ultimately to control the rolling resistance and traction of the other tyres in accordance with punctured tyres to compensate difference in rolling resistance and traction levels. Generally tubeless tyres help in preventing the rapid loss of pressure in puncture scenarios and the SATPOS assist in further enhancing its performance.

According to another aspect, the SATPOS 102 instantaneously works to enhance high speed or extreme cornering characteristic (hard cornering), torque vectoring and vehicle handling characteristic by actively sensing, computing and directing the TPCU 104 to instantaneously control the tyre pressure in right time with right pressure on right tyres thereby preventing & controlling tyres sidewall deformation rate & contact patch while simultaneously providing traction and stability. The SATPOS works in standalone mode or interoperates to enhance the performance of safety and stability systems like TCS, ESC and rollover mitigation systems etcetera. SATPOS restores and optimizes the tyre pressure immediately after the vehicle overcomes the critical situations to continue with safe and comfortable riding.

According to another aspect, the SATPOS 102 sense, compute and direct the TPCU 104 to control and optimize the tyre pressure according to driving modes like comfort, comfort+, standard, economic, sport, sport+ mode etcetera to enhance the comfort level, performance, improving fuel efficiency thereby reducing effect on environment, reduce tyre noise while simultaneously works irrespective of driving modes to instantaneously controlling the tyre pressure accordingly in critical situations to protect and sustain vehicle stability. SATPOS works in standalone mode or interoperates with suspension, safety and stability systems to further enhance the efficiency.

According to another aspect, the SATPOS 102 system works to control and optimize the tyre pressure according to change in centre of gravity and load on each wheel tyres thereby to enhance the stability and handling characteristic of the vehicle. SATPOS either works in standalone mode or Interact with suspension, vehicle safety and stability systems to further enhance the vehicle handling efficiency. SATPOS restores and optimizes the tyre pressure once the load and centre of gravity is restored to continue with safe and comfortable riding.

According to another aspect, the SATPOS particularly utilises one or more high pressure reservoirs (tanks) for storing the fillers like air and nitrogen are optimally located (mounted) on wheel's rim, spoke's, hub, axle etcetera with pneumatic valve and control unit for controlling the tyre pressure in critical situations and optimizing or restoring the tyre pressure after overcoming the critical situations according to the control signal from SATPOS 102. These reservoir systems doesn't need any internal or external compressor systems or other similar sources for controlling the pressure, as the pressure of fillers in the reservoir is already maintained in higher pressure (multiple times) than the optimum tyre pressure for the fillers or fluids to flow from reservoir to tyre thereby to control the tyre pressure accordingly. The reservoir system comprise of container for storing the fillers, pneumatic valve's for controlling the tyre pressure as well as recharging or restoring the fillers, power source for systems operation, air filters, moisture control system, sensor system for monitoring the status of fluids like pressure, temperature, quantity etcetera. The reservoir system comprises of fail-safe and fail-proof pneumatic valves system with actuators and utilise single to multiple internal and external, unidirectional and bidirectional, basic and electro pneumatic valves, valves with & without actuators, normally open & normally closed valves, dedicated & common valves for storing, controlling, optimizing and restoring the tyre pressure according to design, configurations and scenarios. The reservoir system comprise of control system with internal pneumatic valve that connects the reservoir with tyre internally for controlling the tyre pressure and external valves for controlling as well as recharging the fillers. SATPOS utilise either common or dedicated valves for controlling the tyre pressure as well as restoring the fillers. The control valves are selected from pneumatic valves, electro pneumatic valve, mechanical valve, electro mechanical valve, hydraulic valves and its combinations. The reservoir system comprise of dedicated sensor system for sensing the pressure, temperature, moisture and humidity of the fillers available in the reservoir with status of the sensor system being updated to SATPOS for computation and user display or interface. The SATPOS also accounts the quantity of fillers' available in the reservoir with sensor system parameters for the computations of controlling and restoring the tyre pressure. As there are lot of complications with vehicles integrated or inbuilt compressor and similar systems that consumes the valuable space and power also adding extra weight to the vehicle which makes SATPOS more expensive, complex to—operate, integrate, maintain and service; the SATPOS utilised high pressure reservoir without any compressor or similar systems that helps to simplify the operation and overcomes the complications with compressor systems. The SATPOS alerts the driver regarding lack of fillers, component status, and low pressure in reservoir. In scenarios of reservoir with not sufficient fillers or pressure SATPOS alerts the driver regarding the same and operate in default mode where SATPOS won't utilise fillers in the reservoir to control the tyre pressure. The FIGS. 3 A&B describes reservoir system and fluid lines configurations comprise of dedicated inbuilt or integrated reservoir with TPCU 104 on all wheel tires, utilise common reservoir, utilise common reservoir for recharging the fillers of dedicated reservoir and its combinations. The reservoir systems and fluid lines are optimally are designed and integrated according to design of wheels and are either fixed or interchangeable with the wheels. The TPCU 104 utilises either common or dedicated high pressure reservoir according to design and scenarios. The fillers for the reservoir are recharged or restored during or similar to filling the tyre pressure but with higher pressure. The reservoir and its control systems and pneumatic valves are designed to withstand high pressure in different temperature, humidity and moisture. The TPCU with reservoir aids in scenarios where someone had intentionally or playfully deflated the tyres by helping to inflate the tyres with fillers in the reservoir thereby to continue with driving. As the control and access to SATPOS, TPCU & reservoir systems are limited to unauthenticated and outsiders the actual user when back and turn on the vehicle can restore or mitigate situation by controlling the tyre pressure through user interface of the SATPOS. The SATPOS instantaneously controls the tyre pressure through high pressure reservoirs are utilised in active vehicle protection in critical situations, dynamically increasing traction according to driving conditions, optimizing stability, saving fuel and reducing tyre noise.

According to another aspect of the SATPOS, the TPCU comprise of integrated compressor or pump powered by kinetic brake energy—in combination with high pressure fluid reservoir to recharge reservoir fluid and in turn the reservoir restores the tyre pressure or without high pressure reservoir system for directly recharging tyre pressure or its combinations thereby to restore and optimize the tyre pressure ultimately to provide maintenance free operation of tires. The users don't need to maintain or restore the tyre pressure as the SATPOS itself will autonomously work to recharge and maintain the optimum tyre pressure. FIG. 6 A is a block diagram describes the working principle of the SATPOS. The SATPOS utilise Kinetic brake energy generated during braking is either converted into electrical energy or converted into mechanical energy or its combinations according to design, configurations and scenarios and are utilised to run the pump or compressor ultimately for recharging, restoring and optimizing the tyre pressure and the reservoir pressure. The whole system smartly monitors, senses, computes and operates in optimal or right energy band and conditions to utilise the kinetic brake energy based on sensor system parameters, thereby efficiently handling lower and higher or excessively generated kinetic brake energy. The computation is performed based on intensity or level of kinetic brake energy, reservoirs and tyres—internal and external pressure, temperature and moisture, engine and vehicle running conditions thereby accordingly computes, runs and controls the pump or compressor (DEL—pneumatic valves) ultimately to recharge, restore and optimize the reservoir pressure and tyre pressure. The fail-safe and fail-proof pneumatic and (or) electro pneumatic valves with pump &(or) compressor are utilised to ensure safe operations in the event of failure (by operating in fail-safe mode and default mode). Over Pressure release valve or electro pneumatic valve works to release over pressure in reservoir and tires. Either dedicated over pressure protection valve or electro pneumatic valve or its combination is also used. The whole system interoperates with SATPOS to efficiently varies, control, recharge, restore and optimize the pressure in tyres and reservoirs according design, configuration and scenarios.

According to another aspect of the SATPOS, the TPCU utilise kinetic brake energy to run the pneumatic valves thereby to control or transfer the fluid like air, nitrogen etcetera flow from & to or between atmosphere, pump, compressor, reservoirs and tyres or its combinations according design, configuration, requirement and scenarios ultimately to restore and optimize the tyre and reservoir pressure. FIG. 6 B is a block diagram describes the working principle of SATPOS utilise Kinetic brake energy generated during braking is either converted into electrical energy or converted into mechanical energy or its combinations according to design, configurations and scenarios and are utilised to run and control the pneumatic valves ultimately for recharging, restoring and optimizing the tyre pressure and reservoir pressure. The whole system smartly monitors, senses, computes and operates in optimal or right energy band and conditions to utilise the kinetic brake energy based on sensor system parameters, thereby efficiently handling lower and higher or excessively generated kinetic brake energy. The computation is performed based on intensity or level of kinetic brake energy, reservoirs and tyres—internal and external pressure, temperature and moisture, engine and vehicle running conditions thereby accordingly computes, runs and controls the pneumatic valves ultimately to recharge, restore and optimize the reservoir pressure and tyre pressure. The fail-safe and fail-proof pneumatic and (or) electro pneumatic valves with pump & (or) compressor are utilised to ensure safe operations in the event of failure (by operating in fail-safe mode and default mode). Over Pressure release valve or electro pneumatic valve works to release over pressure in reservoir and tires. Either dedicated over pressure protection valve or electro pneumatic valve or its combination is also used. The whole system interoperates with SATPOS to efficiently varies, control, recharge, restore and optimize the pressure in tyres and reservoirs according design, configuration and scenarios.

According to another aspect, the SATPOS in extreme worst case scenarios that comprises of malfunction, partial or complete failure of vehicle safety and stability system (Example—failure of brakes, TCS, rollover mitigation system etcetera) occurs either the on-board system automatically sense the failure to trigger SATPOS or the SATPOS is manually triggered to instantaneously control the tyre pressure for increasing the friction, traction and rolling resistance ultimately to reduce the stopping distance while simultaneously sustaining the vehicle stability, drivability and steer-ability. The SATPOS utilise sensor system and radar system to automatically sense control the tyre pressure according to scenarios. SATPOS assists in brake-failure or malfunction comprising of partial or complete brake failure and either one or multiple brake failure; where maintaining the constant pressure won't assist in reducing the stopping distance.

According to another aspect, the SATPOS 102 works with TPCU 104 integrated with the Active Tyre Temperature Optimizing System (ATTOS) that monitors and senses the change in temperature of weather and environment with present tyre temperature and pressure there by to controls and optimize the tyre temperature and pressure accordingly to improve traction, reduce braking distance (emergency or normal according to scenario), enhance cornering & handling characteristics, mitigate hydroplaning, mitigate over steering and under steering. The tyre compound plays an important role in traction, braking distance, structural stability etcetera which in turn is influenced by tyre temperature. The ATTOS controls the tyre temperature instantaneously in critical situation or continuously according to design, configuration and scenarios. The ATTOS operate in standalone mode or interoperate the SATPOS taking status of power backup in to account. The ATTOS operate in standalone mode interoperate with vehicles safety and stability systems or its combinations according to design, configurations and scenarios to enhance traction and stability. All tyres have an optimum operating temperature and the property of tyre compound varies according to change in temperature. When they reach it the rubber compound is at its stickiest and the carcass at its most flexible. Below that temperature, traction is reduced and the tyre may have a tendency to slide; as the temperature reduces tyre compound becomes harder reducing the traction thereby increasing the braking distance and affecting vehicle handling characteristics. All weather tyres and particularly summer tyres under goes more solidification or hardening than winter tyres when exposed to extremely low environment temperature (winter) and these hardened tyres can have negative impact like increasing the braking distance and loss of traction. There are scenarios where the driver could not predict the sudden change in weather or not in a feasible situation to change the vehicle tyres accordingly or frequently to match with change in weather or environmental conditions thereby to achieve optimized performance—Example—generally the winter tyres are recommended in winter to provide optimum performance in braking distance, driving comfort etcetera on wet, snow and slippery road surface or pavement.

The SATPOS actively controls the tyre temperature thereby controls the tyres property, softening, hardening and controlling sidewall deformation rate ultimately to enhance traction, stability and handling characteristic according to scenarios. The SATPOS controls the tyre temperature either instantaneously in critical situations or continuously according to design, configuration and scenarios. For example—In environments like winter, wet, snow and slippery surfaces etcetera the SATPOS increase and maintains the tyre temperature accordingly to prevent tyres form getting harder or solidification thereby to enhance traction and stability. The SATPOS utilise correlation or lookup tables to actively check and compare the effects caused in actual real world scenarios with predetermined and tested real world scenarios thereby to control and optimize the tyre temperature and pressure according to design, configuration and scenarios. The SATPOS accounts status of power source, sensor system parameters, heating element, change in temperature, moisture & pressure of tyres and environment, driving modes, rim or wheel and tyre specification & parameters comprising of—size, type, load index, speed symbol or rating, thread wear & tear, traction & temperature rating, tyres dimension, direction, nature of compound & material used, maximum load rating, maximum permissible inflation pressure, patterns of treads, lugs, voids, sipes & groves, vehicle safety and stability systems, change in temperature, pressure, moisture and humidity of fillers in reservoirs and compressors for actively sensing, computing the tyre temperature and controlling the tyre temperature. The ATTOS works in both pneumatic and non-pneumatic tires.

The Active Tyre Temperature Optimizing System (ATTOS) works with and utilise either one or combination of direct and indirect heating techniques that comprise of thermal conduction, diffusion, convection, radiation and advection to generate, control and maintain the tyre temperature. Energy transfer and heating elements are optimally integrated in wheels, tires, hub, axel, suspension, vehicles chassis etcetera. The direct heating works utilising heating elements and the indirect heating generate and maintain temperature through heating fillers or fluids & principle of electromagnetic induction heating that operates irrespective of vehicle in stationary or motion according to design, configurations and scenarios. SATPOS make use of Induction heating coil and materials that support electromagnetic induction to generate and maintain heat are utilised in tyre manufacturing that comprises one or combination of ferromagnetic metals, ferromagnetic alloys and other suitable metals or element in fabrication of tires, radial tires, plies, steel belted tyres etcetera thereby to precisely transfer the heat to contact path or foot print area simultaneously saving power. Either dedicated heating element or the plies or belts with suitable material is utilised for induction heating. The TPCU integrated with ATTOS accounts controlling the tyre pressure to an optimum value according to change in temperature to further enhances traction & stability—since controlling of tyre pressure increases or controls the contact patch or footprint surface area with the road thereby further enhancing traction through increasing and controlling the tyre temperature. Generally SATPOS helps in enhancing traction, stability and performance of all tyres and particularly other non-winter tyres like summer tires, all weather tyres etcetera in winter, snow and wet conditions. The TPOS utilise one or more or combination of internal or external power source according to design, configurations and scenarios for controlling and maintaining the temperature. The ATTOS operate in standalone mode with either dedicated power source or interoperate with vehicle power source or its combinations taking status power backup in to account. Regenerative brakes (Kinetic Energy Recovery System or Brake Energy Recuperation System) braking energy can be utilise to control tyre temperature. There are scenarios where excess power available with the vehicle and to avoid over charging these powers are not consumed and this excess available power are utilised by SATPOS for controlling the tyre temperature, also according to scenarios SATPOS maintains threshold level to prevent excess power consumption form vehicles power source. SATPOS is highly user configurable and SATPOS maintains temperature either automatically or manually according to design, configurations and scenarios.

According to another aspect the SATPOS utilise inbuilt sensor system to actively scan, sense, compute and alerts the driver irrespective of vehicles in motion or stationary regarding structural damage on wheels or rims comprising of bends & cracks and potentially hazardous foreign objects (Example—stones) stuck in tyres based on its nature, dimension & depth of penetration, tyres wear & tear, tyre cuts, bulges, sidewall damages, slow puncture with corresponding tyres location & position. The SATPOS utilise smart and adaptive closed loop processing algorithm with correlation or lookup tables to actively check and compare the effects caused in actual real world scenarios with predetermined and tested real world scenarios for precisely sensing, comparing, computing and alerting the driver in advance regarding the potentially hazardous critical situations. SATPOS works based on online and preloaded wheel & rim specifications, balancing beads, tyre specifications & parameters comprising of—size, type, load index, speed symbol or rating, thread wear & tear, traction & temperature rating, compound & material used, maximum load rating, maximum permissible inflation pressure, patterns of treads, lugs, voids, sipes & groves. The SATPOS utilise one or more optimally located internal and external sensors or sensor arrays on wheel tyres and vehicle for scanning comprising of distance or range sensors, visual cameras, IR cameras & sensors, acoustic or ultrasonic sensor, electromagnetic sensors, electrostatic sensors, inductive sensors, capacitive sensors, echo sensors, thermal sensors for scanning & detecting wheels, balancing beads and tyre parameters comprising of specifications, change in properties (nature), patterns, direction, dimension, positions, multi layers and range. The SATPOS works by sensing wheel specifications and nature or property of tyres and foreign objects comprise of permittivity-$\in$, permeability-$\mu$, conductivity-$\sigma$, susceptibility, dielectric, capacitive sensing, capacitive displacement sensing, inductive sensing.

Figure 2:
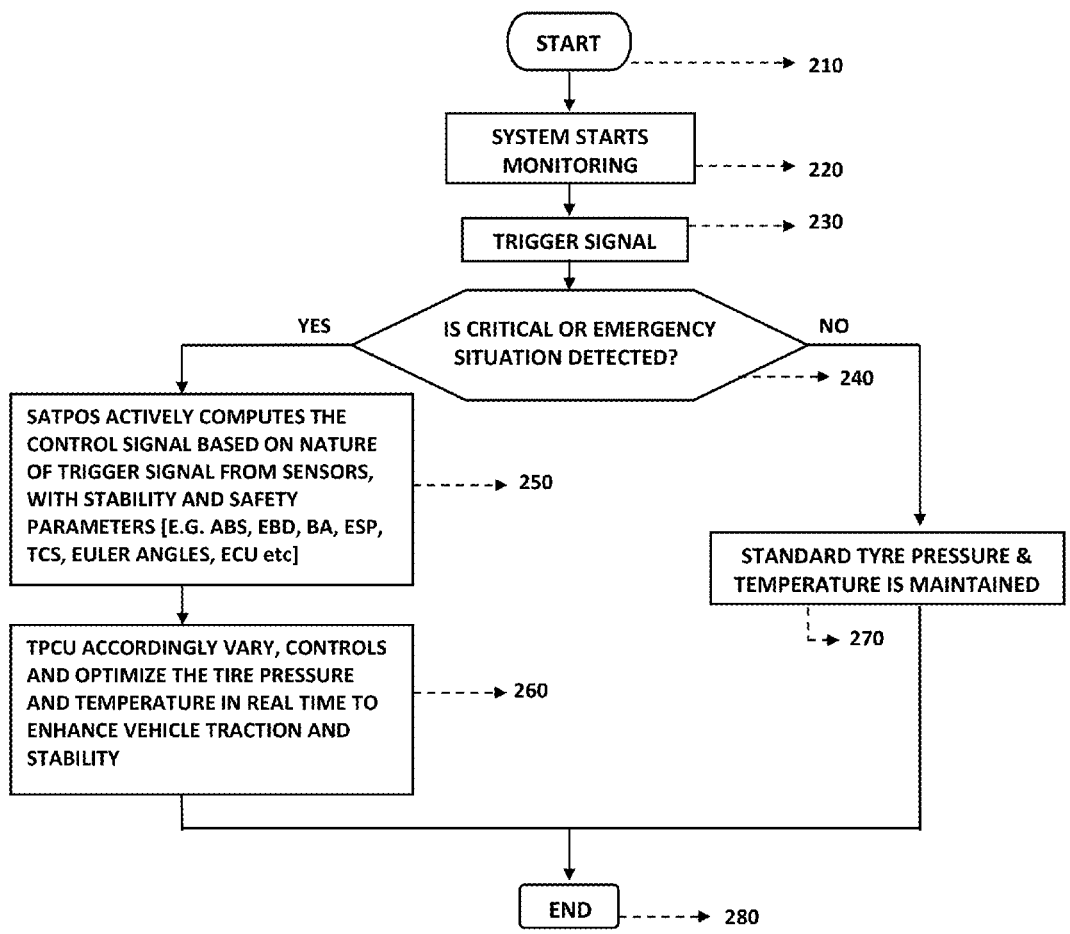
FIG. 2 illustrates the flowchart and describes the method of operation of the smart active tyre pressure optimizing system.

FIG. 2 is the flowchart describes the operation of the SATPOS. By starting with 210 the sensor system 220 monitors the parameters comprising of sensing pressure, temperature, moisture, humidity of fillers available in tyres as well as reservoirs, sensing nature of brake force, sensing vehicle and wheel speed, sensing vehicles orientation, acceleration and deceleration, sensing vehicles load and load on each wheel tires, sensing steering angle or position with vehicles relative motion, sensing objects in the environment of the vehicle with its direction, dimension, nature, approaching & departing speed with respect the vehicle, sensing nature of road, terrain or contact area, utilise GPS sensors for predicting the turns, curves and bends ahead etcetera and accordingly generate the trigger signal 230. The SATPOS analyse the state of trigger signal to compute and detect the critical situation, matching parameters and scenarios to decide on further action 240. The SATPOS actively compute the control signal based on nature of trigger signal 230, safety & stability parameters like ABS, EBD, BA, ESP, TCS, EULER ANGLES, ECU, automotive aerodynamics & airbrakes etcetera and predetermined and tested correlation or mapping table to precisely sensing the critical situations with its effects thereby to control the tyre pressure in an active, adoptive and closed loop manner to overcome and mitigate the critical situations 250. Based on the control signal from SATPOS the TPCU 260 actively controls and optimize the tyre pressure in right time on right tyre with right pressure to reduce the braking distance, overcome and mitigate the critical situations and to restore & sustain vehicle stability 260. In case of no critical situations is detected or not matches any parameters and scenarios SATPOS maintains standard tyre pressure and won't work on controlling temperature 270 according to pre-set configuration and ends with 280.

FIG. 4. Is the flowchart describing the method of operation of SATPOS utilising Kinetic Brake Energy to run the Pump and (or) Compressor to restore and maintain tyre and reservoir pressure according to the SATPOS. By starting with 310 the sensor system 220 monitors the parameters comprising of sensing pressure, temperature, moisture, humidity of fillers available in tyres as well as reservoirs, sensing nature of brake force, sensing vehicle and wheel speed, sensing vehicles orientation, acceleration and deceleration, sensing vehicles load and load on each wheel tires, sensing steering angle or position with vehicles relative motion, sensing objects in the environment of the vehicle with its direction, dimension, nature, approaching & departing speed with respect the vehicle, sensing nature of road, terrain or contact area, utilise GPS sensors for predicting the turns, curves and bends ahead etcetera and accordingly generate the trigger signal 230. SATPOS analyse the state of trigger signal to compute and detect whether the tyre and reservoir pressure sufficient to decide on further action 340. In case of insufficient pressure SATPOS monitors the nature of braking 380 with magnitude of kinetic energy. SATPOS analyse whether the Kinetic brake energy is sufficient to run the pump or compressor 390. SATPOS actively computes the control signal based on magnitude and nature of kinetic brake energy, safety & stability parameters like ABS, EBD, BA, ESP, TCS, EULER ANGLES, ECU, automotive aerodynamics & airbrakes etcetera and predetermined and tested correlation or mapping table to precisely sensing effects thereby directs the TPCU to act accordingly 360. Based on the control signal from SATPOS the TPCU 370 actively controls and runs the integrated pump or compressor to recharge, restore and optimize the tyre and reservoir pressure 370. In case of kinetic brake energy not sufficient SATPOS won't run the pump or compressor and maintains the available tyre and reservoir pressure 370 according to pre-set configuration and ends with 410.

FIG. 5. is the flowchart describing the method of operation of SATPOS utilising Kinetic Brake Energy to run the Pneumatic valves for fluid transfer thereby to restore and maintain tyre and reservoir pressure according to the SATPOS. By starting with 310 the sensor system 220 monitors the parameters comprising of sensing pressure, temperature, moisture, humidity of fillers available in tyres as well as reservoirs, sensing nature of brake force, sensing vehicle and wheel speed, sensing vehicles orientation, acceleration and deceleration, sensing vehicles load and load on each wheel tires, sensing steering angle or position with vehicles relative motion, sensing objects in the environment of the vehicle with its direction, dimension, nature, approaching & departing speed with respect the vehicle, sensing nature of road, terrain or contact area, utilise GPS sensors for predicting the turns, curves and bends ahead etcetera and accordingly generate the trigger signal 230. SATPOS analyse the state of trigger signal to compute and detect whether the tyre and reservoir pressure sufficient to decide on further action 340. In case of insufficient pressure SATPOS monitors the nature of braking 380 with magnitude of kinetic energy. SATPOS analyse whether the Kinetic brake energy is sufficient to run the pneumatic valves 590. The SATPOS actively computes the control signal based on magnitude and nature of kinetic brake energy, safety & stability parameters like ABS, EBD, BA, ESP, TCS, EULER ANGLES, ECU, automotive aerodynamics & airbrakes etcetera and predetermined and tested correlation or mapping table to precisely sensing effects thereby directs the TPCU to act accordingly 560. Based on the control signal from SATPOS the TPCU 370 actively controls and runs the pneumatic valves to transfer fluids ultimately to recharge, restore and optimize the tyre and reservoir pressure 570. In case of kinetic brake energy not sufficient SATPOS won't run the pneumatic valves and maintains the available tyre and reservoir pressure 550 according to pre-set configuration and ends with 610.

The TPCU 104 comprises of internal or external power source for its operation and is selected from TPCU's inbuilt batteries, capacitors and vehicle batteries. The power source is wired or wireless and the charging sources for the TPCU's inbuilt battery and capacitor are sourced from vehicle battery, external charging systems, internal self-charging systems with feasible alternator or generator, capacitive coupling, inductive coupling, electromagnetic coupling etcetera. The type of batteries utilised comprise of primary batteries or rechargeable batteries, Regenerative brakes [Kinetic Energy Recovery System or Brake Energy Recuperation System] or its combinations. The power source is internal fixed or replaceable, external and its combinations with SATPOS smartly managing the charging and backup [Example—under & over charging protection] of the power levels with updating & alerting the status of power source to SATPOS, display and user interface. In case on both capacitor and battery utilised, according design configuration and scenarios SATPOS utilise the battery to power the monitoring system for sensing and updating the status of tyre pressure, temperature, RF transmission etcetera and the capacitor can be utilised to instantaneously supply the power to electro pneumatic valve actuator (for controlling the tyre air pressure according to the trigger from SATPOS). The SATPOS tap's the required power for its operation according to vehicle's running conditions and engine parameters (Example—vehicle running down the slope or declined roads with excess speeds where the cruise control system controls the excess speed to maintain pre-set speed).

The SATPOS 102 comprise of sensor system that works based on one or combination of sensors, safety & stability parameters, configurations, operating modes and usage scenarios for detecting the critical situations of vehicles experiencing or moving beyond the limits of vehicles available safety and stability systems with sensors for active sensing and utilise it for pre-computing & set ready to control tyre pressure, current-computing to control the tyre pressure during critical situation and post-computing to control the tyre pressure after critical situation ultimately to overcome and mitigate the critical situations—1. Sensors for sensor system comprise of Pressure sensors, Temperature sensors, humidity and moisture sensors for sensing the pressure, temperature, humidity and moisture content of fluids or fillers available in tyres and reservoirs. The sensor system in addition senses the external or environments temperature, moisture and humidity for computation thereby to enhance the precision of SATPOS; 2. Vehicle speed and wheel speed sensor for sensing the vehicle speed and wheels speed thereby sensing the loss of traction and wheel slip or spin ultimately for computing the tyre pressure accordingly in critical situations; 3. Orientation sensors and accelerometer for sensing the vehicles orientation, acceleration and deceleration ultimately for computing the tyre pressure accordingly in critical situations; 4. Load sensor for sensing the load of the vehicle, load on individual wheel tyres and change in centre of gravity ultimately for computing the tyre pressure accordingly in critical situations; 5. Steering angle or position sensor for sensing the position of the steering wheel and vehicles relative motion thereby sensing vehicle stability, over and under steering ultimately for computing the tyre pressure accordingly in critical situations; 6. Brake force sensor for sensing the nature of the brake force during braking scenarios ultimately for pre-computing, current-computing and post-computing thereby to control the tyre pressure accordingly in critical situation in critical situations; 7. Sensors for sensing tyre properties and foreign objects stuck in tire, dimension & depth of penetration, tyres wear & tear, tyres cuts, bulges, sidewall damages, slow puncture with corresponding tyres location & position comprise of distance or range sensors, visual cameras, IR cameras, acoustic or ultrasonic sensor, electromagnetic sensors, electrostatic sensors, inductive sensors, capacitive sensors, echo sensors, thermal sensors. SATPOS utilise one or more optimally located internal and external sensors or sensor arrays on tyres and vehicle for scanning comprising of distance or range sensors, visual cameras, IR cameras, acoustic or ultrasonic sensor, electromagnetic sensors, electrostatic sensors, inductive sensors, capacitive sensors, echo sensors, thermal sensors for scanning & detecting tyres parameters comprising of change in tyre properties (nature), patterns, direction, dimension, positions, multi layers & range, pressure, temperature, moisture and humidity. The sensor sensing the nature or property of tyre and foreign object comprise of permittivity-$\in$, permeability-$\mu$, conductivity-$\sigma$, susceptibility, dielectric, capacitive sensing, capacitive displacement sensing, inductive sensing; 8. Radar and range sensors for scanning the environment around the vehicle by detecting vehicles, pedestrians and objects in front, rear and around the vehicle with its direction, dimension, nature, approaching & departing speed with respect the vehicle thereby utilised for pre-computing, current-computing and post-computing ultimately for controlling the tyre pressure according to critical situation. The radar system comprises of visual, active and passive infrared cameras with real-time digital image and signal processing thereby to sense the nature of the objects around the vehicle; 9. Terrain, road or contact area sensors for sensing the nature of present contact and impending road and terrain surfaces with its property comprising of normal dry roads, wet, mud & ruts, rocks, gravel, grass, snow, sand, rough, highly uneven terrain, rocky crawl and its combinations thereby computing the tyre pressure accordingly in critical situations; 10. GPS sensors for predicting the turns, curves and bends ahead of the road for pre-computing and set ready for action in controlling the tyre pressure accordingly; 11. The SATPOS utilises predetermined and tested field mapping or lookup table for sensing, comparing & matching the effects between real time sensor system parameters with predetermined and tested sensor system parameters ultimately for computing the tyre pressure accordingly; 12. The sensor systems precision levels, sensing depth of dimension and multi-layer sensing are utilised depends upon the design & requirement. The sensor system utilise sensors, with either fixed or tuneable sensitivity and the range are selected according to design, scenarios and requirement.

The SATPOS 102 utilise correlation or lookup tables to actively check and compare the effects caused in actual real world scenarios with predetermined and tested real world scenarios to control and optimizing the tyre pressure accordingly in critical situations. The tables comprise of pressure values that lies between upper and lower cut-off tyre pressure values designed and developed with corresponding change in vehicles load and centre of gravity thereby the SATPOS 102 controls the tyre pressure between upper and lower cut-off tyre pressure values according to scenarios to mitigate critical situations while preventing the over inflation and deflation or tyre deformation ultimately to sustain stability. The table is designed and developed based on SATPOS designs, scenarios, configurations and parameters comprising of—sensor system, vehicle stability & safety systems, nature of braking &brake force, tyres lower & upper cut-off threshold pressure values, sensing reservoirs and tyres internal & external or environmental—pressure, temperature, moisture, humidity, vehicles speed, wheel speed, acceleration & deceleration, orientations & axial rotation (yaw, pitch and roll), load distribution (load on each wheel tire), torque distribution, vehicles suspension & vertical dynamics, transverse motion & lateral acceleration, tyre traction, slip and slide angle, steering wheel position, cornering effects, change in centre of gravity, over & under steering, aqua or hydroplaning, rim or wheel specifications, wheel alignment & balancing, tyre specifications & parameters comprising of—size, type, load index, speed symbol or rating, thread wear & tear, traction & temperature rating, compound & material used, maximum load rating, maximum permissible inflation pressure, direction, dimension, patterns of treads, lugs, voids, sipes & groves, tyres position or angle of attack, Coefficient of Friction (COF), radars detecting objects with pre-computing & current-computing of tyre pressure to assist in emergency braking& stability based on range, direction and dimension of objects in and around the vehicle, sensing nature of tyres present & impending contact area, GPS information to predict the turns, curves and bends on roads ahead and inter operating with vehicles existing stability & safety systems comprising of—ABS, EBD, ESC, TCS, Roll over mitigation systems, ECU, BA, Pre-crash systems, suspension system, vertical dynamics & damping force, Sway or anti-roll or stabilizer bar, radar assisted auto braking with partially & complete brake to stop, Drivers reaction with evasion (evasive manoeuvre) of objects, automotive aerodynamics & airbrakes, Pre-crash systems, Cruise or Adaptive Cruise Control with partial & full auto braking. As various parameters and multiple critical situations are simultaneously taken into account by SATPOS for computation, the table is designed and developed based on prioritising and balancing between one or more parameters and scenarios ultimately to achieve an optimized performance.

With self-supporting reinforced tyres the efficiency of the SATPOS is further enhanced where these tyres have an additional supporting ring attached to the wheel that can support the weight of the vehicle in the event of a loss of pressure. For Example—Run-flat tyres (RFT) have specially reinforced side walls and additional lateral strengthening helps continue to perform their function even if all air pressure is lost. The heat-resistant rubber compounds are able to withstand additional heat build-up and the wheel rims of run-flat tyres have special design that ensures the tyre will not detach from the rim, even on tight bends. The SATPOS also assists in reducing the braking or stopping distance of aircrafts—landing or take-off on runway in critical situations like abort take-off, rejected take-off due to over running of runway for take-off, emergency landing, reducing stopping distance in brake failure etcetera which can sometimes leads to aircraft moving beyond safety margin and the available runway may be insufficient to stop the aircraft. The wheel tyres with TPCU are constructed with a counterweight or utilise externally added tyre weights (balance) to compensate the mass of the TPCU. The precisely well-equipped SATPOS helps in mitigating the negative effects caused by vehicles utilising mixed tyres like old & new tires, different thread pattern tyres and different types like wet & dry tyres, Soft & hard compound tyres, slick & intermediate tires, summer & winter tyres with various patterns off treads, lugs, voids, grooves etcetera thereby by ultimately enhancing the overall performance.

The embodiments of the SATPOS is not limited to listed scenarios described here or its combinations and the above presented are just examples. There may be other scenarios and those who skilled in field can understand and, modify, enhance, alter the herein system without departing from the scope of the invention in its widest form.

The invention claimed is:

1. A Smart Active Tyre Pressure Optimizing System (SATPOS) for vehicles, comprising:
   a) a sensor system for actively monitoring, sensing and generating trigger signal to SATPOS by detecting the vehicle's critical situations comprising:
   high speed and emergency braking;
   loss of traction;
   hydroplaning or aquaplaning;
   loss of stability;
   rollover;
   over and under steering;
   puncture;
   b) a processing unit Smart Active Tyre Pressure Optimizing System (SATPOS) is a highly time sensitive design and technique with very high processing and functioning speeds that autonomously and instantaneously sense and controls the tyre pressure particularly during imminent and inevitable critical driving situations to
   reduce emergency and high speed braking distance;
   mitigate hydroplaning;
   mitigate loss of traction;
   mitigate roll over;
   mitigate loss of stability and control;
   mitigate over and under steering;
   mitigate loss of control due to puncture;
   through real-time sensing, perform context aware computing and directing the Tyre Pressure Control Units (TPCU) on each wheel tire to actively vary, control, optimize and restore the tyre pressure in right time with right pressure on right tyres thereby instantaneously controlling the tyre's contact patch or footprint area and sidewall deformation rate to enhance traction and stability while sustaining vehicle's drivability or steer-ability thereby to avoid or reduce the impact of collision and to overcome or mitigate the critical situations to protect occupants, vehicles, pedestrians and other things around and on the way;
   c) the TPCU that instantaneously acts according to the control signal from the SATPOS which is located on each wheel tyre to instantly vary and control the tyre pressure in right time with right pressure on right tyres thereby to actively enhance or optimize traction and sustain stability comprising:
   sensor system;
   pneumatic valve with actuators;
   transceivers and antennas;
   power source;
   reservoirs;
   Active Tyre Temperature Optimizing System (ATTOS) and
   heating elements wherein
   the TPCU actively shares sensor system parameters and components status with the SATPOS; the controlling of tyre pressure is preformed either simultaneously on all the tyres or any particular tyres according to scenarios and control signal from the SATPOS;
   d) the SATPOS performs active monitoring and sensing, pre-computing and set ready to control the tyre pressure prior to critical situation, current-computing to control the tyre pressure during critical situation, post-computing to immediately restore or optimize tyre pressure after overcoming the critical situations to continue with comfortable driving, enhanced stability, enhanced mileage and reduced tyre noise;
   e) the SATPOS utilise smart and adaptive closed loop processing algorithm with correlation or lookup table to instantaneously check and compare the effects between predetermined and tested real world scenarios and parameters to the actual real world scenarios for smart and actively—sensing, computing and controlling the tyre pressure accordingly to mitigate the critical situations; the SATPOS either controls the pressure by releasing the fillers such as air or nitrogen to atmosphere while maintaining the tyre's lower cut off threshold pressure value where the pneumatic valve's automatically closes when lower cut off tyre pressure value is reached which is above the minimum tyre pressure value to sustain stability and instantaneously optimize the pressure on all tyres for further safe driving till next gas station or filling until restoration or else restores the pressure to optimum pre-set value utilising inbuilt reservoir or external restoration system immediately after the vehicle overcomes critical situation to continue with comfortable driving.

2. The SATPOS in said claim 1, comprise of sensor system that works based on one or combination of sensors, safety and stability parameters, configurations, operating modes and usage scenarios for detecting the critical situations of vehicles experiencing or moving beyond the limits of vehicles available safety and stability systems comprising:
  a) pressure sensors;
  temperature sensors;
  humidity and moisture sensors for sensing the pressure, temperature, humidity and moisture content of fluids or fillers available in tyres and reservoirs respectively; the sensor system also senses the external or environments temperature, moisture and humidity for computation thereby to enhance the precision of the SATPOS;
  vehicle speed and wheel speed sensor;
  b) orientation sensors and accelerometer for sensing the vehicles orientation, acceleration and deceleration;
  d. Load c) load sensor for sensing the load of the vehicle, load on individual wheel tyres and change in centre of gravity;
  d) steering angle or position sensor for sensing the position of the steering wheel and vehicles relative motion thereby sensing vehicle stability, over and under steering;
  e) brake force sensor;
  f) sensors for sensing damage in wheels, tyre properties and foreign objects stuck in tire, its dimension and depth of penetration, tyres wear and tear, tyres cuts, bulges, sidewall damages, slow puncture with corresponding tyres location and position comprise of one or more optimally located internal and external sensors or sensor arrays on tyres and vehicle for scanning comprising of distance or range sensors, visual cameras, Infrared (IR) cameras, acoustic or ultrasonic sensor, electromagnetic sensors, electrostatic sensors, inductive sensors, capacitive sensors, echo sensors, thermal sensors for scanning and detecting tyres parameters comprising of change in tyre properties, patterns, direction, dimension, positions, multi-layers and range, pressure, temperature, moisture and humidity; the sensor sensing the nature or property of tyre and foreign object comprise of permittivity $\in$, permeability $\mu$, conductivity $\sigma$, susceptibility, dielectric, capacitive sensing, capacitive displacement sensing, inductive sensing;
  g) radar and range sensors for scanning the environment around the vehicle by detecting vehicles, pedestrians and objects in front, rear and around the vehicle with its direction, dimension, distance, nature, approaching and departing speed with respect to the vehicle; the radar system comprises of visual, active and passive infrared cameras with real time digital image and signal processing thereby to sense the nature of the objects around the vehicle;
  h) terrain, road or contact area sensors for sensing the nature of present contact and impending road and terrain surfaces with its property comprising of normal dry roads, wet, mud and ruts, rocks, gravel, grass, snow, sand, rough, highly uneven terrain, rocky crawl and its combinations;
  i) Global Positioning System (GPS), location and positioning sensors for predicting the turns, curves and bends ahead of the road.

3. The SATPOS in said claim 1, where the SATPOS comprising:
  processing unit;
  transceiver;
  antennas;
  interconnections with sensor systems;
  Engine Control Unit (ECU);
  vehicle stability and safety parameters;
  memory; and
  online access for live updates wherein
  the SATPOS actively computes the control signal to control the tyre pressure based on either one or combination of the following
  a) the SATPOS computation and controlling of tyre temperature and pressure in critical situations are within the scope or range of tyres upper and lower cut off threshold values thereby to prevent over or under inflation of tyre and to sustains vehicle stability;
  b) the SATPOS computation of control signal to TPCU's utilises parameters comprising:
  sensor system;
  vehicle stability and safety systems;
  nature of braking and brake force;
  tyres lower and upper cut off threshold pressure values where lower cut off pressure is above the minimum tyre pressure value;
  sensing reservoirs and tyres internal and external or environmental pressure, temperature, moisture, humidity;
  vehicles speed;
  wheel speed;
  acceleration and deceleration;
  orientations and axial rotation comprising yaw, pitch and roll;
  load distribution which means load on each wheel tire;
  torque distribution;
  vehicles suspension and vertical dynamic;
  transverse motion and lateral acceleration;
  tyre traction;
  Coefficient of Friction (COF);
  slip and slide angle, steering wheel position;
  cornering effects;
  change in centre of gravity;
  over and under steering;
  aqua or hydroplaning;
  radars detecting objects with pre-computing and current-computing of tyre pressure to assist in emergency braking and stability based on range, direction and dimension of objects in and around the vehicle;
  tyre specifications and parameters comprising of size, type, load index, speed symbol or rating, thread wear and tear, traction and temperature rating, tyres dimension, direction, compound and material used, maximum load rating, maximum permissible inflation pressure, patterns of treads, lugs, voids, sipes and groves, rim or wheel specifications;
  camber angle;
  wheel alignment and balancing;
  tyres position or angle of attack;
  terrain sensing detecting nature of tyres present and impending contact area;
  GPS information to predict the turns, curves and bends on roads ahead;
  c) the SATPOS also inter operate with vehicles existing stability and safety systems comprising:
  Anti-lock Braking System (ABS);
  Electronic Brake-force Distribution (EBD);
  Electronic Stability Control (ESC);

Traction Control System (TCS);
Roll over mitigation systems;
ECU;
Brake Assist (BA);
Pre-crash systems;
suspension system;
vertical dynamics and damping force;
sway or anti roll or stabilizer bar;
radar assisted auto braking with partially and complete brake to stop;
automotive aerodynamics and airbrakes;
sensing drivers reaction with evasion manoeuvre of objects; and
cruise or adaptive cruise control with partial and full auto braking
thereby instantaneously directing the TPCU to control the tyre pressure on corresponding tyres in right time to overcome or mitigate the critical situations; as various parameters and multiple critical situations are simultaneously taken into account by SATPOS for computation, the SATPOS's algorithm smartly sense, prioritise and balance between one or more parameters and scenarios to achieve the optimized solution;
d) the SATPOS either operates in standalone mode with sensor system parameters or interoperates with vehicles stability and safety parameters or its combinations to enhancing traction and stability in critical situation; the controlling of tyre pressure is either even or uneven and continuous or discontinuous on all tyres according to design, configurations and scenarios;
e) the SATPOS performs self-diagnostic or test to verify and conform regarding the working of components and accessibility of corresponding parameters; in case of crucial parameters inaccessible and components failure the SATPOS will operate in fail-proof or fail-safe mode and default mode to ensure safe operation; in scenarios of further controlling of tyre pressure is not possible due to component failure, lack of fillers or pressure and lack of power to run, the SATPOS alerts the driver regarding the same and works in default mode to retain the available or even or optimum pressure on all tires;
f) the SATPOS works with or without or combination of internal or external high pressure reservoirs and compressor systems for instantaneously controlling and optimizing the tyre pressure during and after overcoming the critical situations;
g) the SATPOS utilise the TPCU integrated with the ATTOS to control the tyre temperature according to change in temperature of environments or weather and in critical situations by controlling tyres properties, preventing tyre hardening or solidification thereby to enhances tyre traction, stability, reduce braking distance, enhance vehicle cornering and handling characteristics, mitigate hydroplaning, mitigate over steering and under steering; the SATPOS controls the tyre temperature either instantaneously in critical situations or continuously.

4. The SATPOS in said claim 1, where the TPCU is located in each wheel tire, hub and axel comprising:
pneumatic valve with actuators;
controller circuitry for controlling tyre pressure according to control signal from the SATPOS;
transceiver;
antennas;
sensors;
power source;
fluid reservoir system;
integrated pump and compressor;
ATTOS; and
heating elements wherein
a) the TPCU shares the real time information and parameters such as tyre pressure, temperature, humidity, moisture, power source status, reservoir status with SATPOS and act according to control signal from the SATPOS thereby to control the tyre pressure and temperature;
b) the TPCU utilise fail-safe and fail-proof pneumatic valves system with actuators for controlling the tyre pressure according to control signal from the SATPOS; the TPCU comprise of and utilise wheel tyres integrated with single to multiple internal and external, unidirectional and bidirectional, valves with and without actuators, normally open and normally closed valves, basic and electro pneumatic valves, dedicated and common valves for storing, controlling, optimizing and restoring the tyre pressure according to design, configurations and scenarios;
c) the TPCU utilise wireless transceiver with antenna, wired communication and its combinations for communicating with the SATPOS;
d) the TPCU comprise of internal power source, external power source and its combinations for its operation and are selected from the TPCU's inbuilt batteries, capacitors and vehicle batteries; the power source is wired or wireless or its combinations and the charging sources for the TPCU's inbuilt battery and capacitor are sourced from vehicle battery, external charging systems, internal self-charging systems with feasible alternator or generator, capacitive coupling, inductive coupling, electromagnetic coupling and regenerative brakes; the type of batteries utilised comprise of primary batteries, rechargeable batteries and its combinations;
e) the power source is either external, internal fixed or replaceable and its combinations with the TPCU smartly managing the charging and backup of the power levels with updating and alerting the status of power source to the SATPOS, display and user interface;
f) the TPCU works with and without, internal and external, reservoir and compressor or its combinations for instantaneously controlling and optimizing the tyre pressure during and after overcoming the critical situations; in critical situations the TPCU controls the tyre pressure by either releasing the fillers to atmosphere and restore from internal and external reservoir and compressor or store and restore the fillers from and to internal and external reservoir and compressor according to design, configurations and scenarios;
g) the TPCU with reservoir works by instantaneously controlling and optimizing the tyre pressure during and after overcoming the critical situations utilising the high pressure fillers in the reservoir; the TPCU comprise of control system with internal pneumatic valve that connects the reservoir with tyre internally for controlling the tyre pressure and external valve for controlling as well as recharging the fillers;
h) the TPCU utilise either common or dedicated valves for controlling the tyre pressure as well as restoring the fillers; the control valves are selected from pneumatic valves, electro pneumatic valves, mechanical valves, electro mechanical valves and its combinations;
i) the TPCU with compressor works by instantaneously controlling and optimizing the tyre pressure during and after overcoming the critical situations utilising the fillers from compressor unit;

j) the TPCU works without reservoir or compressor through instantaneously controlling the tyre pressure in critical situations by releasing the fluids or fillers like air or nitrogen to the atmosphere and optimizes the tyre pressure on all tyres for further safe driving;

k) the TPCU comprise of integrated ATTOS and heating elements for maintaining the temperature according to control signal from the SATPOS;

l) each TPCU is represented by unique identification with which the SATPOS identifies and communicate with accordingly; the SATPOS also accounts the replacement of tyres to precisely track the change of tyres in scenarios of puncture, wear and tear thereby to control the TPCU accordingly;

m) the SATPOS also optimizes the tyre pressure on the spare tyre to match with other tyres in case of tyre changed according to scenarios;

n) the TPCU instantaneously controls the tyre pressure in critical situations by controlling or transferring the fillers either from and to atmosphere else with inbuilt or external restoration systems or its combinations;

o) the TPCU utilise feasible internal or external reservoir or its combination for controlling the fillers thereby instantaneously controlling the tyre pressure in critical situations;

p) the TPCU utilise feasible internal or external air compressor or its combination for controlling the fillers thereby instantaneously controlling the tyre pressure in critical situations;

q) the TPCU sense and prevents the over inflation of tyres by releasing excess fillers thereby to maintain the set and optimum pressure according to control signal from the SATPOS;

r) the wheels with TPCU are constructed with weight balanced design or with counterweight and utilise internal and externally added weights to balance or compensate the mass of the TPCU.

5. The SATPOS in said claim 1, utilise correlation or lookup tables to actively check and compare the effects caused in actual real world scenarios with predetermined and tested real world scenarios to control and optimizing the tyre pressure in critical situations comprising:

a.) the correlation tables comprise of pressure values that lies between upper and lower cut off tyre pressure values designed and developed with corresponding change in vehicles load and centre of gravity;

b) the correlation table is designed and developed based on the SATPOS designs, scenarios, configurations and parameters comprising:

sensor system;
vehicle stability and safety systems;
nature of braking and brake force;
tyres lower and upper cut off threshold pressure values;
sensing reservoirs and tyres internal and external or environmental pressure;
temperature;
moisture;
humidity;
vehicles speed;
wheel speed;
acceleration and deceleration;
orientations and axial rotation comprising yaw, pitch and roll;
load distribution on each wheel tire;
torque distribution;
vehicles suspension and vertical dynamic;
transverse motion and lateral acceleration,
tyre traction;
COF;
slip and slide angle;
steering wheel position;
cornering effects;
change in centre of gravity;
over and under steering;
aqua or hydroplaning;
tyre specifications and parameters comprising of size, type, load index, speed symbol or rating, thread wear and tear, traction and temperature rating, compound and material used, maximum load rating, maximum permissible inflation pressure, direction, dimension, patterns of treads, lugs, voids, sipes and groves;
rim and wheel specifications;
camber angle;
wheel alignment and balancing;
tyres position or angle of attack;
radars detecting objects with pre-computing and current-computing of tyre pressure to assist in emergency braking and stability based on range, direction and dimension of objects in and around the vehicle;
sensing nature of tyres present and impending contact area;
GPS information to predict the turns, curves and bends on roads ahead;
inter operating with vehicles existing stability and safety systems comprising:
ABS;
EBD;
ESC;
TCS;
Roll over mitigation systems;
ECU;
BA;
Pre-crash systems;
suspension system;
vertical dynamics and damping force;
sway or anti roll or stabilizer bar;
radar assisted auto braking with partially and complete brake to stop;
automotive aerodynamics and airbrakes;
sensing drivers reaction with evasion manoeuvre of objects; and
cruise or adaptive cruise control with partial and full auto braking;

c) as various parameters and multiple critical situations are simultaneously taken into account by the SATPOS for computation, the table is designed and developed based on prioritising and balancing between one or more parameters and scenarios ultimately to achieve an optimized performance.

6. The SATPOS in said claim 1, where the SATPOS instantaneously works in critical situation to reduce high speed and emergency braking distance by actively sensing, computing and controlling the tyre pressure from optimum or existing value to right pressure on right tyres in right time ultimately to increase the rolling resistance, friction and controlling contact patch area thereby instantaneously improving traction while sustaining stability.

7. The SATPOS in said claim 1, where the SATPOS works in critical situations to instantaneously mitigate extreme loss of traction, skid and wheel spin on either one or multiple wheel tyres by actively sensing, computing and controlling the tyre pressure between or corresponding wheel tyres in right time with right pressure thereby controlling the contact patch or foot print ultimately to restore and mitigate loss of traction.

8. The SATPOS in said claim 1, where the SATPOS works in critical situations to instantaneously mitigate hydroplaning or aquaplaning by actively sensing, computing and controlling by increasing the tyre pressure on right tyres with right pressure in right time while maintaining the tyres upper cut off threshold pressure value thereby thinning the contact path surface area of tyre to avoid water deflected inwards, increasing the tyres grooves and thread depth to deflect more water outward ultimately helping in clearing water which in turn prevents the rising of tyres thereby to mitigate hydroplaning.

9. The SATPOS in said claim 1, where the SATPOS works in critical situations to instantaneously mitigate over and under steering by actively sensing, computing and controlling the tyre pressure in right time with right pressure on right tyres thereby controlling thread depth, enhancing traction, controlling contact patch or foot print area, controlling tyres cornering stiffness and controlling tyre deformation rate thereby mitigating positive and negative gradient to sustain zero or neutral gradient.

10. The SATPOS in said claim 1, where the SATPOS works in critical situations to mitigate roll over and loss of stability for the vehicle moving in highly uneven, leaning, slope surfaces, vehicle experience high speed and extreme cornering force where the vehicle tends to move beyond available stability systems limits that can leads to loss of stability by actively sensing and instantaneously controlling the tyre pressure on right tyres with right pressure in right time thereby to restore stability, centre of gravity and traction.

11. The SATPOS in said claim 1, where the SATPOS works in critical situations to mitigate the loss of control and stability in puncture scenarios besides alerting the driver regarding rapid loss of pressure in puncture scenarios by actively sensing and instantaneously supplying the fillers like air or nitrogen from the reservoir or tank to the punctured tyres thereby to sustain the pressure preventing the rapid loss of tyre pressure ultimately improving the time of drivability and stability of the vehicle wherein
   a) in puncture, the SATPOS controls the pressure on other tyres accordingly to enhance the drivability and stability of the vehicle;
   ) in puncture, the SATPOS controls and reduces the pressure on other tyres accordingly to increase the rolling resistance thereby reducing the braking distance of vehicles in high speeds scenarios;
   c) the SATPOS actively works to control tyre pressure ultimately to control the rolling resistance and traction of the other tyres in accordance with punctured tyres to mitigate difference in rolling resistance and traction levels.

12. The SATPOS in said claim 1, instantaneously works to enhance extreme and high speed or hard cornering performance, torque vectoring and handling characteristic by instantaneously sensing, computing and controlling the tyre pressure in right time with right pressure on right tyres thereby assists in enhancing sharp cornering characteristic through preventing and controlling tyres sidewall deformation and contact patch area while simultaneously providing traction and stability.

13. The SATPOS in said claim 1, vary, control and optimize the tyre pressure according to driving modes like comfort, comfort+, standard, economic, sport, sport+ mode to enhance the comfort level, performance, improving fuel efficiency thereby reducing effect on environment according to modes, controlling tyre noise and in addition works irrespective of modes to instantaneously control the tyre pressure accordingly to mitigate critical situations.

14. The SATPOS in said claim 1, vary, control and optimize the tyre pressure according to change in centre of gravity and load on each wheel tyres by sensing, computing and controlling or optimizing the tyres accordingly to enhance vehicle stability and handling characteristic.

15. The SATPOS in said claim 1, utilise the TPCU integrated with the ATTOS that works to control and maintain the tyre temperature and pressure according to change in temperature of weather or environment and critical situations thereby actively controlling the tyres property, softening, hardening or solidification, controlling contact patch area and sidewall deformation rate ultimately to enhance tyre traction, stability, reduce braking distance, enhance cornering and handling characteristics, mitigate hydroplaning, mitigate over steering and under steering wherein
   a) the SATPOS utilise smart and adaptive closed loop algorithm with correlation or lookup tables to actively check and compare the effects caused in actual real world scenarios with predetermined and tested real world scenarios thereby to control and optimizing the tyre temperature and pressure according to design, configuration and scenarios;
   b) the SATPOS controls the tyre temperature either instantaneously in critical situations or continuously;
   c) the ATTOS operate in standalone mode interoperate with vehicles safety and stability systems or its combinations to enhance traction and stability;
   d) the SATPOS utilise one or more or combination of internal or external power source according to design, configurations and scenarios for controlling and maintaining the temperature;
   e) the ATTOS operate in standalone mode with either dedicated power source or interoperate with vehicle power source or its combinations taking status power backup in to account;
   e. The Tire Temperature Optimising System (TTOS]f) the ATTOS works with and utilise either one or combination of direct and indirect heating techniques that comprise of thermal conduction, diffusion, convection, radiation and advection to generate, control and maintain the tyre temperature;
   g) energy transfer and heating elements are optimally integrated in wheels, tires, hub, axel, suspension and vehicles chassis; the direct heating works utilising heating elements and the indirect heating generate and maintain temperature through heating fillers or fluids and principle of electromagnetic induction heating that operates irrespective of vehicle in stationary or motion according to design, configurations and scenarios;
   h) the SATPOS make use of Induction heating coil and materials that support electromagnetic induction to generate heat are utilised in tyre manufacturing that comprises one or combination of ferromagnetic metals, ferromagnetic alloys and other suitable metals or element in tires, radial tires, plies and steel belted tyres thereby to precisely transfer the heat to contact path or foot print area simultaneously saving power; either dedicated heating element or the plies or belts with suitable material is utilised for induction heating;
   f. The system i) the SATPOS accounts status of power source, sensor system parameters, heating element, change in temperature, moisture and pressure of tyres and environment, driving modes, rim or wheel and tyre specification and parameters comprising of size, type, load index, speed symbol or rating, thread wear and tear, traction and temperature rating, tyres dimension, direction, nature of compound and material used, maximum load rating, maximum permissible inflation pressure, patterns of treads, lugs, voids, sipes and groves, vehicle safety and stability systems, change in temperature, pressure, moisture and humidity of fillers in reservoirs and compressors for actively sensing, computing and controlling the tyre temperature;

j) the ATTOS works in both pneumatic and non-pneumatic tires;

k) the SATPOS operates in standalone mode or interoperates the SATPOS taking status of power backup in to account.

16. The SATPOS in said claim 1, where the SATPOS utilise inbuilt sensor system to actively scan, sense, compute and alerts the driver irrespective of vehicles in motion or stationary regarding structural damage on wheels or rims comprising of bends and cracks and potentially hazardous foreign objects; for instance stones stuck in tyres based on its nature, dimension and depth of penetration, tyres wear and tear, tyre cuts, bulges, sidewall damages, slow puncture with corresponding tyres location and position wherein a) the SATPOS utilise smart and adaptive closed loop processing algorithm with correlation or lookup tables to actively check and compare the effects caused in actual real world scenarios with predetermined and tested real world scenarios for precisely sensing, comparing, computing and alerting the driver in advance regarding the potentially hazardous critical situations;

b) the SATPOS works based on online and preloaded wheel or rim specifications, balancing beads, tyre specifications and parameters comprising of size, type, load index, speed symbol or rating, thread wear and tear, traction and temperature rating, compound and material used, maximum load rating, maximum permissible inflation pressure, patterns of treads, lugs, voids, sipes and groves;

c) the SATPOS utilise one or more optimally located internal and external sensors or sensor arrays on wheel tyres and vehicle for scanning comprising of distance or range sensors, visual cameras, IR sensors and cameras, acoustic or ultrasonic sensor, electromagnetic sensors, electrostatic sensors, inductive sensors, capacitive sensors, echo sensors, thermal sensors for scanning and detecting wheels, balancing beads and tyre parameters comprising of specifications, change in properties, patterns, direction, dimension, positions, multi-layers and range;

c. The system d) the SATPOS works by sensing wheel specifications and nature or property of tyres and foreign objects comprise of permittivity c, permeability p, conductivity a, susceptibility, dielectric, capacitive sensing, capacitive displacement sensing, inductive sensing.

17. The SATPOS in said claim 1, where the SATPOS works with all types of tyres comprising:
pneumatic tyres comprising of tubeless tires, non-tubeless or tyres with tubes;
non-pneumatic tires;
Run Flat Tyres (RFT);
wet tires;
dry tires;
soft and hard compound tires;
slick tires;
intermediate tires;
summer tires; and winter tyres
with various patterns off treads, lugs, voids, grooves, sipes, beads, sidewalls, shoulders, plies.

18. The SATPOS in said claim 1, works with all type of vehicles comprising motor cycles, cars, vans, Sports Utility Vehicle (SUV), cross over, buses, trucks or lorries, aircrafts with single to multiple pneumatic tyres utilising air, nitrogen or other suitable fillers.

19. The SATPOS in said claim 1, works in critical situation with following configurations comprising of one or more combinations with reservoir, without reservoir and appropriate compressor systems wherein a) the SATPOS works in critical situations with reservoir by utilising the high pressure fillers in the reservoir to control the tyre pressure; where the fillers in the reservoir have to be restored from external sources;

b) the SATPOS works in critical situations without reservoir or compressor by just releasing the fillers in the tyres to atmosphere and the tyre pressure have to be restored through external sources;

c) the SATPOS works in critical situations with appropriate compressor systems available with vehicles existing inflation systems in critical situations.

20. The SATPOS in said claim 1, where the SATPOS instantaneously works in extreme worst case scenarios such as malfunction, partial or complete failure of vehicle safety and stability system comprising:
brake failure or brake malfunction with partial or complete brake failure and either one or multiple brake failure;
traction control system;
rollover mitigation system;
the on board system automatically sense the failure and triggers the SATPOS.

21. The SATPOS in said claim 1, comprises of the TPCU integrated with appropriate compressor or pump powered by kinetic brake energy in combination with high pressure fluid reservoir to recharge reservoir fluid and in turn the reservoir restores the tyre pressure or without high pressure reservoir system for directly recharging tyre pressure or its combinations thereby autonomously works to restore and optimize the tyre pressure ultimately to provide maintenance free operation of tires; the TPCU interoperates with the SATPOS where the compressor or pump system works based on either one or combinations comprising:

b. Pump or [&] Compressor a) pump or compressor system works with high pressure reservoir system to recharges, restore and optimize reservoir pressure and in turn the high pressure reservoir system works to recharge, restore and optimize the tyre pressure;

b) pump or compressor system works without high pressure reservoir system by directly recharging, restoring and optimizing the tyre pressure;)

) the SATPOS utilise kinetic brake energy generated during braking which is either converted into electrical or mechanical energy or its combinations and are utilised to run the pump or compressor ultimately for recharging, restoring and optimizing the tyre pressure and the reservoir pressure;

d) the SATPOS smartly monitors, senses, computes and operates in optimal or right energy band to utilise the kinetic brake energy thereby efficiently handling lower and higher or excessively generated kinetic brake energy;

e) the computation is performed based on intensity or level or magnitude of kinetic brake energy, reservoir's and tire's internal and external pressure, temperature and moisture, engine and vehicle's running conditions thereby accordingly computes, runs and controls the pump or compressor ultimately to recharge, restore and optimize the reservoir pressure and tyre pressure;

f) the fail-safe and fail-proof pneumatic or electro pneumatic valves with pump or compressor are utilised to ensure safe operations in the event of failure by operating in fail-safe mode and default mode;
g) over pressure release valve or electro pneumatic valve works to release over pressure in reservoir and tires; either dedicated over pressure protection valve or electro pneumatic valve or its combinations are utilised by the SATPOS.

22. The SATPOS in said claim 1, comprises of the TPCU utilising kinetic brake energy to run the pneumatic valves thereby to control or transfer the fluid like air, nitrogen flow from and to or between atmosphere, pump, compressor, reservoirs and tyres or its combinations according to design, configuration, requirement and scenarios ultimately to restore and optimize the tyre and reservoir pressure; the SATPOS monitors and computes the kinetic or brake energy that is sufficient to run or operate the pneumatic valves; the SATPOS and the TPCU controls the operation of pneumatic valves based on either one or combination of following according to design, configurations and scenarios wherein
) the SATPOS utilise kinetic brake energy generated during braking which is either converted into electrical or mechanical energy or its combinations and are utilised to run and control the pneumatic valves;
b. The whole system b) the SATPOS smartly monitors, senses, computes and operates in optimal or right energy band and conditions to utilise the kinetic brake energy based on sensor system parameters, thereby efficiently handling lower and higher or excessively generated kinetic brake energy;
c) the computation is performed based on intensity or level or magnitude of kinetic brake energy, reservoir's and tire's internal and external pressure, temperature and moisture, engine and vehicle's running conditions thereby accordingly computes, runs and controls the pneumatic valves;
c. The system d) the SATPOS utilise fail-safe and fail-proof electro mechanical pneumatic valves that acts in default operation or valve mode with basic valve functionality to ensure safe operation in case of failure.

23. The SATPOS in said claim 1, comprise of one or more or combination of internal and external, fixed or replaceable power source for the SATPOS and the TPCU's operation are selected from the TPCU's inbuilt batteries, primary or rechargeable batteries, capacitors and vehicle batteries according to design, configurations and scenarios wherein
a) the power source is wired or wireless or its combinations and the charging sources for the TPCU's inbuilt battery and capacitor are sourced from vehicle battery, external charging systems, internal self-charging systems with feasible alternator or generator, piezoelectric effect, capacitive coupling, inductive coupling, electromagnetic coupling, kinetic brake energy;
b) the SATPOS smartly manages the charging and backup for instance under and over charging protection of the power levels with updating and alerting the status of power source to the SATPOS, display and user interface;
c) the TPCU tap's the required power for its operation from and based on vehicle's running conditions and engine parameters for instance vehicle running down the slope or declined roads with excess speeds where the cruise control system control the excess speed to maintain preset speed.

24. The TPCU in said claim 1, comprising of one or more particularly high pressure fluid reservoirs or tank for storing the fillers air and nitrogen are integrated or optimally located or mounted on wheel's rim, spoke's, hub, axle with pneumatic valves and control unit that controls the tyre pressure in critical situations and optimizing or restoring the tyre pressure after overcoming the critical situations according to the control signal from the SATPOS; the reservoir systems operates without any compressor or other similar systems as the pressure maintained in the reservoir is higher or multiple times than the optimum tyre pressure for the fluids or fillers to flow from reservoir to tyre thereby controlling the tyre pressure according to control signal from the SATPOS wherein
a) the fillers in the reservoir or tank are maintained with pressure higher or multiple times higher than the upper cut off tyre pressure threshold value for the fillers to instantly flow from the reservoir to tyres and the same is utilised for controlling the tyre pressure according to control signal from the SATPOS; the fillers in the reservoir are restorable and restored through external means similarly restored while filling the normal tyre pressure;
b) the reservoir system comprises of fail-safe and fail-proof pneumatic valves system with actuators and utilise single to multiple internal and external, unidirectional and bidirectional, basic and electro pneumatic valves, valves with and without actuators, normally open and normally closed valves, dedicated and common valves for storing, controlling, optimizing and restoring the tyre pressure according to design, configurations and scenarios;
c) the reservoir comprise of control system with internal pneumatic valve that connects the reservoir with tyre internally for controlling the tyre pressure and external valve for controlling as well as recharging the fillers;
d) the valve system utilise either common or dedicated valves for controlling the tyre pressure as well as restoring the fillers;
e) the control valves are selected from pneumatic valves, electro pneumatic valve, mechanical valve, electro mechanical valve and its combinations;
f) the reservoir system comprise of dedicated sensor system for sensing the pressure, temperature, moisture and humidity of the fillers available in the reservoir with status of the sensor system being updated to the SATPOS for computation and user display or interface;
g) the SATPOS also accounts the quantity of fillers available in the reservoir with sensor system parameters for the computations, controlling and restoring the tyre pressure;
h) the SATPOS alerts the driver regarding lack of fillers and low pressure in reservoir; in scenarios of reservoir with not sufficient fillers or pressure the SATPOS alerts the driver regarding the same and works in default mode where the SATPOS won't utilise fillers in the reservoir to control the tyre pressure;
i) the reservoir utilise moisture control system to remove excess moisture and maintain optimum moisture level of fillers in reservoir thereby to achieve optimum SATPOS operations;
j) the reservoir system configurations comprise of dedicated inbuilt or integrated reservoir with the TPCU on all the wheel tires, utilise common reservoir, utilise common reservoir for recharging the fillers of dedicated reservoir and its combinations for controlling and optimizing the tyre pressure;
k) the SATPOS comprise of air filter and moisture control system to maintain the ideal state of fluids or fillers for achieving optimum performance;
l) the reservoir system is optimally designed and integrated according design of wheels and are either fixed or interchangeable with the wheels;

m) the TPCU utilises either common or dedicated high pressure reservoir according to design and scenarios;
n) controlling of tyre pressure with reservoir system is performed based on configurations comprising of releasing the fillers to atmosphere and controlling or restoring through fillers in the reservoir or else controlling through storing and restoring of fillers from and to reservoir according to design and scenarios;
o) the SATPOS with instantaneously controlling the tyre pressure through high pressure reservoirs are utilised on active vehicle protection in critical situations, dynamically increasing traction according to driving conditions, optimizing stability, saving fuel and reducing tyre noise;
p) the SATPOS utilise the fillers in the high pressure reservoir to optimize the tyre pressure in under inflation scenarios.

* * * * *